(12) United States Patent
Benson et al.

(10) Patent No.: US 12,000,515 B2
(45) Date of Patent: Jun. 4, 2024

(54) FLUID COUPLINGS

(71) Applicant: Colder Products Company, Roseville, MN (US)

(72) Inventors: Timothy Charles Benson, Andover, MN (US); Randall S. Williams, Minneapolis, MN (US); Andrew M. Quick, Saint Paul, MN (US)

(73) Assignee: Colder Products Company, Roseville, MN (US)

( * ) Notice: Subject to any disclaimer, the term of this patent is extended or adjusted under 35 U.S.C. 154(b) by 94 days.

(21) Appl. No.: 17/412,921

(22) Filed: Aug. 26, 2021

(65) Prior Publication Data

US 2022/0065377 A1 Mar. 3, 2022

Related U.S. Application Data

(60) Provisional application No. 63/071,006, filed on Aug. 27, 2020.

(51) Int. Cl.
*A61M 39/18* (2006.01)
*F16L 37/26* (2006.01)

(52) U.S. Cl.
CPC ............ *F16L 37/26* (2013.01); *A61M 39/18* (2013.01)

(58) Field of Classification Search
CPC .......... A61M 39/10; A61M 2039/1066; A61M 2039/1027; A61M 2039/1088; A61M 39/20; A61M 39/28; A61M 39/284; F16L 2201/44
See application file for complete search history.

(56) References Cited

U.S. PATENT DOCUMENTS

| | | | |
|---|---|---|---|
| 4,334,551 A | 6/1982 | Pfister | |
| 4,429,713 A | 2/1984 | Walter | |
| 4,429,852 A | 2/1984 | Tersteegen et al. | |
| 4,502,701 A | 3/1985 | Treloar et al. | |
| 4,664,148 A | 5/1987 | Magnuson | |

(Continued)

FOREIGN PATENT DOCUMENTS

| | | |
|---|---|---|
| CN | 103615618 | 3/2014 |
| CN | 203907084 | 10/2014 |

(Continued)

OTHER PUBLICATIONS

International Search Report and Written Opinion in International Appln. No. PCT/US2021/047743, dated Dec. 7, 2021, 11 pages.

(Continued)

*Primary Examiner* — Matthew Troutman
*Assistant Examiner* — Alexander T Rufrano
(74) *Attorney, Agent, or Firm* — Fish & Richardson P.C.

(57) ABSTRACT

Fluid coupling devices can be configured for use in fluid systems for purposes of providing a single-use, aseptic disconnection functionality that can substantially limit fluid spillage when being disconnected. In some embodiments, the coupling portions cannot be functionally reconnected to each other after being disconnected from each other. The coupling portions can be identical to each other in some embodiments. A retainer component of the fluid coupling devices can be removably engaged with the coupling portions while the coupling portions are abutted against each other in an operative arrangement.

20 Claims, 41 Drawing Sheets

(56) References Cited

U.S. PATENT DOCUMENTS

| | | |
|---|---|---|
| 4,804,015 A | 2/1989 | Albinsson |
| 4,950,255 A * | 8/1990 | Brown ................ A61M 39/284 604/533 |
| 4,960,259 A * | 10/1990 | Sunnanvader ........ A61M 39/28 251/7 |
| 5,097,859 A | 3/1992 | Grabenkort et al. |
| 5,257,978 A | 11/1993 | Haber et al. |
| 5,806,564 A | 9/1998 | Wilcox |
| 5,971,019 A | 10/1999 | Imai |
| 6,161,578 A | 12/2000 | Braun et al. |
| 6,237,631 B1 | 5/2001 | Giesler et al. |
| 6,302,147 B1 | 10/2001 | Rose et al. |
| 7,410,155 B2 | 8/2008 | Spain |
| 7,469,472 B2 | 12/2008 | deCler et al. |
| 7,547,047 B2 | 6/2009 | deCler et al. |
| 7,959,192 B2 | 6/2011 | Elton et al. |
| 8,267,370 B2 | 9/2012 | Fisher et al. |
| 8,491,016 B2 * | 7/2013 | Williams ............ A61M 39/18 285/377 |
| 8,690,120 B2 | 4/2014 | Hartnett et al. |
| 8,863,364 B2 | 10/2014 | Gay et al. |
| 8,910,918 B2 | 12/2014 | Gay et al. |
| 9,402,987 B2 | 8/2016 | Kamen et al. |
| 9,726,308 B2 * | 8/2017 | Williams ................ F16L 37/30 |
| 10,022,532 B2 | 7/2018 | Burdge |
| 10,525,249 B2 | 1/2020 | Wegener et al. |
| 10,668,265 B2 | 6/2020 | Burdge |
| 2003/0187379 A1 | 10/2003 | Sun |
| 2007/0073215 A1 | 3/2007 | Wieslander |
| 2008/0185056 A1 | 8/2008 | Diodati et al. |
| 2009/0051161 A1 | 2/2009 | Eskstrom |
| 2009/0076434 A1 | 3/2009 | Mischelevich |
| 2010/0183361 A1 | 7/2010 | Davis |
| 2010/0230950 A1 | 9/2010 | Scott et al. |
| 2011/0006520 A1 * | 1/2011 | Hall ...................... A61M 39/00 285/383 |
| 2011/0240158 A1 | 10/2011 | Py |
| 2012/0031515 A1 | 2/2012 | Whitaker |
| 2013/0341904 A1 | 12/2013 | Lehmann et al. |
| 2014/0345748 A1 | 11/2014 | Rogers et al. |
| 2015/0260325 A1 | 9/2015 | Quick |
| 2016/0158519 A1 | 6/2016 | Rhinehart |
| 2016/0186906 A1 * | 6/2016 | Blake ................ A61M 39/1011 285/319 |
| 2017/0284584 A1 | 10/2017 | Kesselaar et al. |
| 2018/0296817 A1 | 10/2018 | Burdge et al. |
| 2019/0298985 A1 | 10/2019 | Truong |

FOREIGN PATENT DOCUMENTS

| | | |
|---|---|---|
| CN | 204062272 | 12/2014 |
| DE | 202012000597 | 6/2013 |
| EP | 0028601 | 5/1981 |
| GB | 2269224 | 2/1994 |
| WO | WO 1980/001507 | 7/1980 |
| WO | WO 2008/094707 | 8/2008 |
| WO | WO 2012/114105 | 8/2012 |
| WO | WO 2014/160756 | 10/2014 |
| WO | WO 2016/172229 | 10/2016 |
| WO | WO 2017/062859 | 4/2017 |

OTHER PUBLICATIONS

International Preliminary Report on Patentability in International Appln. No. PCT/US2021/047743, dated Mar. 9, 2023, 9 pages.

* cited by examiner

FLUID COUPLINGS

CROSS-REFERENCE TO RELATED APPLICATIONS

This application claims the benefit of U.S. Provisional Application Ser. No. 63/071,006, filed Aug. 27, 2020. The disclosure of the prior application is considered part of (and is incorporated by reference in) the disclosure of this application.

BACKGROUND

1. Technical Field

This document relates to fluid coupling devices for fluid systems and methods. For example, some embodiments described in this document relate to single-use, aseptic disconnection fluid coupling devices.

2. Background Information

Fluid systems commonly include components such as tubing, pumps, reservoirs, fittings, couplings, heat exchangers, sensors, filters, valves, seals, and the like. Such components can be connected together in a network to define one or more fluid flow paths. Some fluid systems are open systems, meaning that the fluid flows through the network once and then exits the network. Other fluid systems are closed systems, meaning that the fluid recirculates within the network of components. Fluids may be moved through fluid systems using fluid pressure differentials. For example, in some cases, a pump or a vacuum source is used to create a pressure differential that causes the fluid to flow within the fluid system. In another example, gravity is used to cause the fluid to flow within the fluid system. In other examples, a combination of such techniques is used to cause the fluid to flow within the fluid system.

In the context of some fluid systems, such as some bioprocessing fluid systems, it may be desirable to have a tube coupler that can aseptically disconnect a fluid flow path. In one such example implementation, it is desirable to disconnect aseptically one or more containers (e.g., media bags) from a bioreactor system. In that scenario, an aseptic coupling can be used to disconnect the container(s) from the bioreactor system while substantially preventing biological contamination of the containers, of tubing, of other connected components, and of the bioreactor via the disconnected ends of the coupling during and after the disconnection process. Such an aseptic coupling will also serve to limit the exposure of the fluid to the surrounding environment.

SUMMARY

This document describes fluid coupling devices for fluid systems and methods. In some embodiments, the fluid coupling devices can be implemented as single-use, aseptic disconnection fluid coupling devices that are configured to reduce the likelihood of fluid spillage when being disconnected. In some embodiments, the coupling portions cannot be reconnected to each other after being disconnected from each other. Accordingly, the fluid coupling devices are called "single-use" disconnect couplings. In the context of this disclosure, the term "fluid" means any substance that can be made to flow including, but is not limited to, liquids, gases, granular or powdered solids, mixtures or emulsions of two or more fluids, suspensions of solids within liquids or gases, etc.

In particular embodiments, the fluid coupling devices described herein are single-use devices because, after the two portions of the coupling (also referred to herein as "coupling halves" and/or "connectors") are disconnected from each other, the fluid paths of one or both portions are irreversibly blocked. Hence, in these particular embodiments, the fluid coupling devices provided herein are structurally configured to be single-use disconnection devices so that, after the single-use coupling halves have been disconnected from each other, they cannot be operably reconnected to each other (or to any other coupling halves) so as to reestablish an open fluid flow path therethrough.

Additionally, in such single-use embodiments or in other embodiments, the fluid coupling devices can be configured as "aseptic" coupling devices in that, during disconnection and after the two portions of the coupling device are disconnected from each other, the fluid paths of both portions are mechanically blocked, e.g., by a valve, so as to inhibit biological contamination migrating into the flow paths. Such an "aseptic" coupling will also serve to limit the exposure of the fluid to the surrounding environment. As used herein, the term "aseptic" refers to any process that maintains a sterilized surface or volume.

In one aspect, this disclosure is directed to a fluid coupling device. For example, this disclosure is directed to a single-use aseptic fluid coupling device that includes a first coupling, a second coupling, and a retainer removably coupled to the first coupling and to the second coupling. The first coupling includes: (i) a first body including a first termination end portion, the first body defining a first seal recess and a first fluid flow path extending through the first body from the first termination end portion to the first seal recess; (ii) a first seal disposed within the first seal recess, the first seal defining a first bore through which the first fluid flow path extends; and (iii) a first closure clip movably coupled to the first body and including a first projection configured to compress the first seal when the first closure clip is pressed into the first body. The second coupling includes: (i) a second body including a second termination end portion, the second body defining a second seal recess and a second fluid flow path extending through the second body from the second termination end portion to the second seal recess; (ii) a second seal disposed within the first seal recess, the second seal defining a second bore through which the second fluid flow path extends; and (iii) a second closure clip movably coupled to the second body and including a second projection configured to compress the second seal when the second closure clip is pressed into the second body. The retainer holds the first and second couplings in contact with each other such that: (i) the first seal abuts against the second seal and (ii) the first fluid flow path and the second fluid flow path are fluidly connected.

Such a fluid coupling device may optionally include one or more of the following features. In some embodiments, the fluid coupling device is reconfigurable from a first configuration to a second configuration. The first bore and the second bore are each fluidly open while the fluid coupling device is in the first configuration, and the first bore and the second bore are each fluidly closed while the fluid coupling device is in the second configuration. In some embodiments, the fluid coupling device is configured such that, when the fluid coupling device is in the second configuration, the fluid coupling device is irreversibly configured in the second configuration. While the fluid coupling device is in the second configuration, the first projection may compress the first seal to fluidly close the first bore and the second projection may compress the second seal to fluidly close the second bore. In some embodiments, the retainer is not removable from the first and second couplings while the fluid coupling device is in the first configuration, and the retainer may be removable from the first and second couplings while the fluid coupling device is in the second configuration. In some embodiments, the first coupling and the second coupling are only separable from each other when: (i) the fluid coupling device is in the second configuration and (ii) the retainer is uncoupled from the first coupling and the second coupling. The fluid coupling device may also include a first cover that is movably coupled to the first body, and a second cover that is movably coupled to the second body. In some embodiments, the fluid coupling device is configured such that when the first and second couplings are separated from each other: (a) the first cover can be moved to cover the first seal within the first seal recess; and (b) the second cover can be moved to cover the second seal within the second seal recess. The first and second couplings may be identical to each other. In some embodiments, the first and second closure clips are removably coupled to each other such that the first and second closure clips are configured to move synchronously relative to the first body and the second body. The fluid coupling device may also include a spacer removably coupled to the fluid coupling device and arranged to prevent relative movement between: (i) the first closure clip and the first body, and (ii) the second closure clip and the second body. The first and second seal recesses may each be shaped as a cylinder and include two open side adjuncts positioned radially of the cylinder. In some embodiments, the first and second seals each comprise two cylindrical end portions and a central portion with a thinner wall than the two cylindrical end portions. The central portion may have an arcuate outer profile and an arcuate inner profile. A center of an arc of the arcuate outer profile may be located in an opposite direction in comparison to a center of an arc of the arcuate inner profile.

In some embodiments, the first and second seals each include a cylindrical end portion that has a larger outer diameter than the other portions of the first and second seals. The first seal may be engaged with an inner nipple of the first body and the second seal may be engaged with an inner nipple of the second body. The fluid coupling device may also include a first cover that is movably coupled to the first closure clip, and a second cover that is movably coupled to the second closure clip. In some embodiments, the first cover includes a projection that is engaged within a recess defined by the second cover, and the second cover includes a projection that is engaged within a recess defined by the first cover. The first cover may include a first plug that projects from the first cover and is configured to fluidly seal the first bore. The second cover may include a second plug that projects from the second cover and is configured to fluidly seal the second bore. In some embodiments, the retainer includes one or more flexible side portions that each include one or more projections that are engaged in one or more recesses defined by the first and second bodies. The one or more projections may disengage from the one or more recesses by depressing the first and second closure clips relative to the first and second bodies.

Particular embodiments of the subject matter described in this document can be implemented to realize one or more of the following advantages. First, the coupling halves of the fluid coupling devices provided herein are designed so that the uncoupling process involves closing valves in a particular sequence so that spillage related to fluid inclusion is eliminated or minimized.

Second, in some embodiments, the fluid coupling devices are designed to have a minimal number of components so that the fluid coupling devices are economical.

Third, some embodiments of the fluid coupling devices provide an improved non-spill disconnection capability.

Fourth, some embodiments of the fluid coupling devices provide an improved aseptic disconnection capability that may optionally reduce or eliminate the need for sterile rooms or sterile benchtop environments in some cases. As such, these embodiments of the aseptic fluid coupling devices described herein may facilitate efficient and cost-effective operations or uses that would otherwise be high-cost or even cost prohibitive in some traditional settings that required the disconnection of particular fluid couplings in a sterile room or within a sterile flow-hood to prevent biological contamination.

Fifth, some embodiments of the fluid coupling devices provided herein are advantageously designed to be single use couplings that cannot be operatively reconnected to reestablish an open flow path therethrough. Accordingly, the potential for contamination from reuse is prevented.

Sixth, some embodiments of the fluid coupling devices provided herein are advantageously designed to be genderless couplings. In this context, genderless means that both coupling halves are of the same design (except perhaps the terminations) and are configured to couple to each other. Such a genderless design can reduce manufacturing costs and reduce the complexity of using the fluid coupling devices.

Seventh, some embodiments of the fluid coupling devices provided herein are a metallic-free construction (also referred to as a nonmetallic fluid coupling device). As such, such embodiments of the nonmetallic fluid coupling devices can be advantageously sterilized using a gamma sterilization technique. Also, in some circumstances, the nonmetallic fluid coupling devices exhibit enhanced fatigue-resistance characteristics, minimal installed stress, and enhanced corrosion resistance in comparison to some fluid couplings that include traditional metallic parts such as metal springs.

Unless otherwise defined, all technical and scientific terms used herein have the same meaning as commonly understood by one of ordinary skill in the art to which this disclosure pertains. In addition, the materials, methods, and examples of the embodiments described herein are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION OF ILLUSTRATIVE EMBODIMENTS

Figure 1:
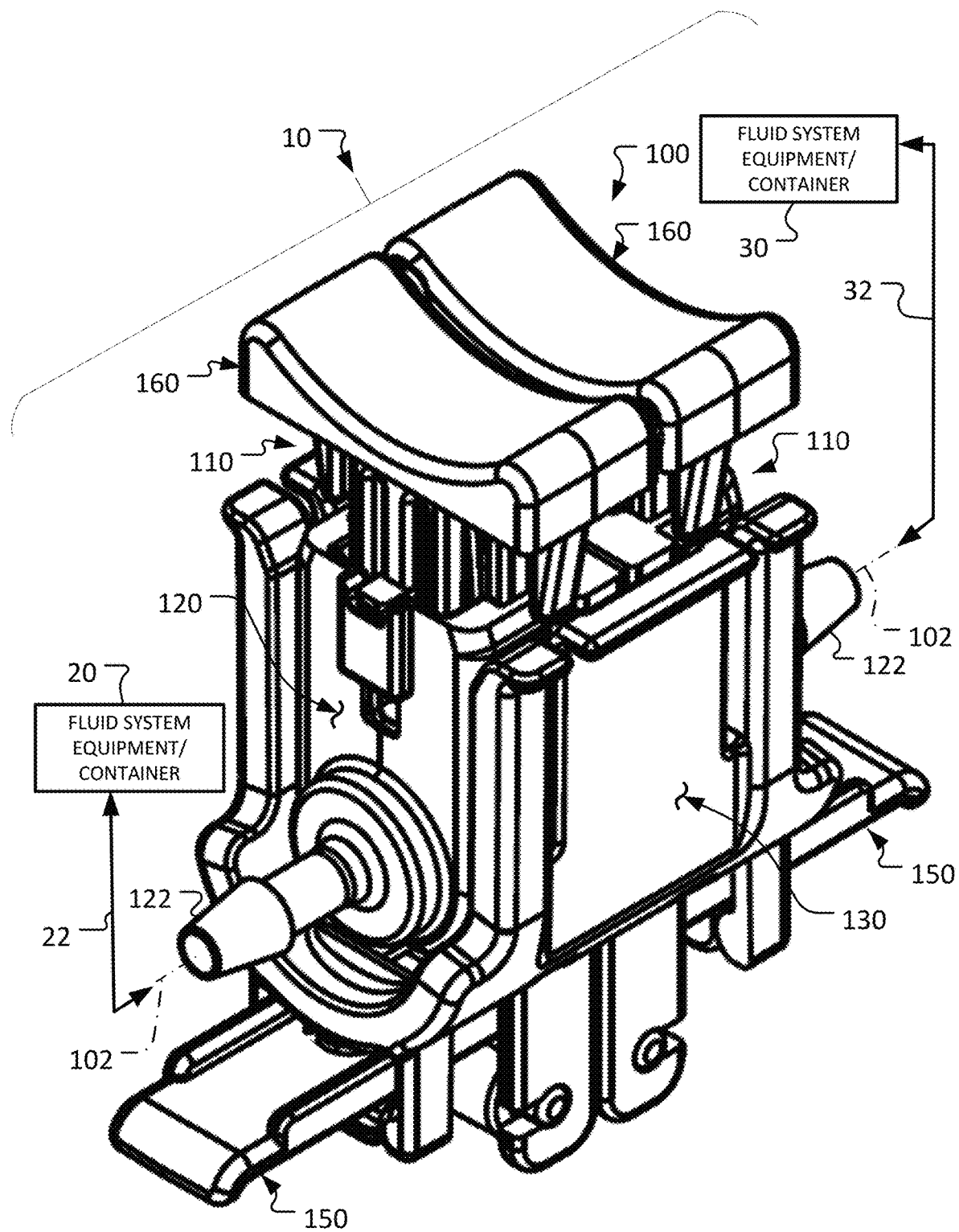
FIG. 1 is a perspective view of an example fluid system including an example fluid coupling device arranged in an operative connected configuration, in accordance with some embodiments provided herein.
Figure 2:
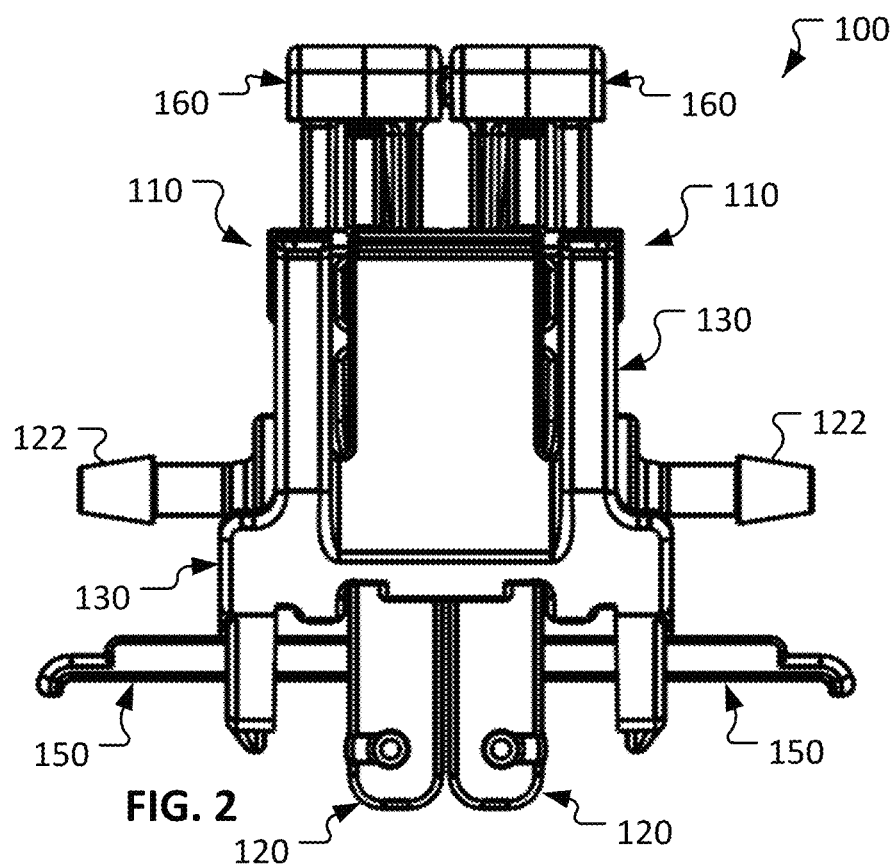
FIG. 2 is a side view of the fluid coupling device of FIG. 1.
Figure 3:
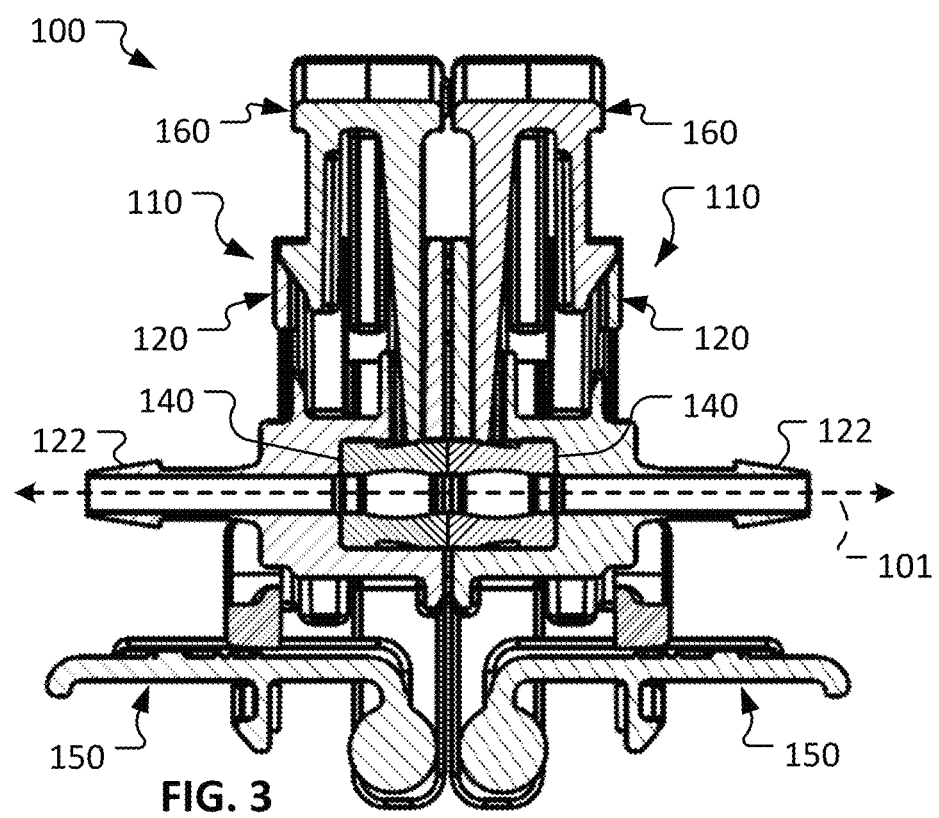
FIG. 3 is a longitudinal cross-sectional view of the fluid coupling device of FIG. 1.
Figure 4:
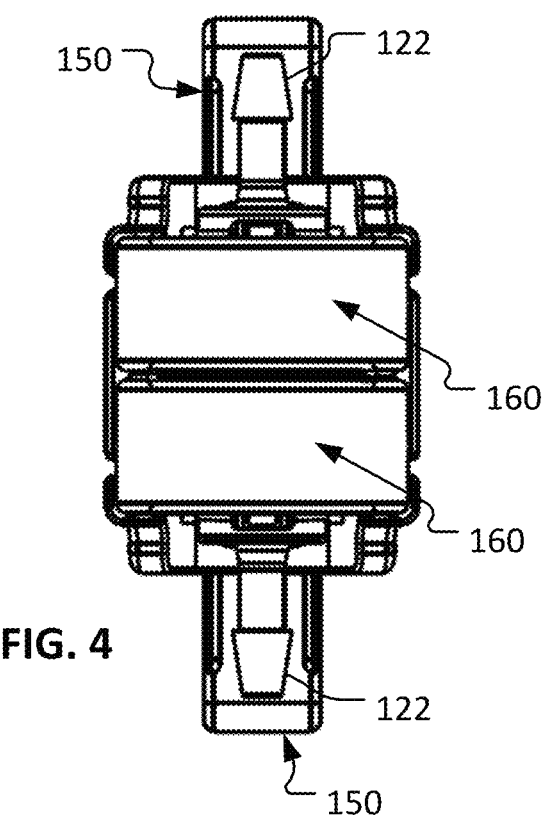
FIG. 4 is a top view of the fluid coupling device of FIG. 1.
Figure 5:
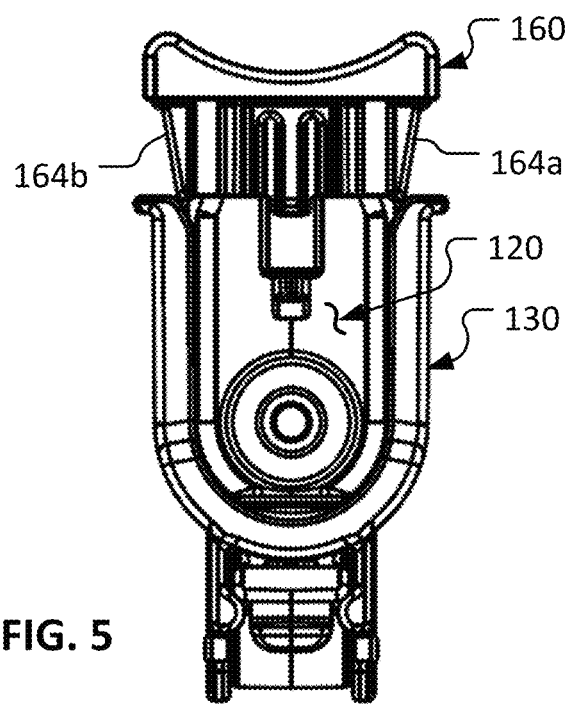
FIG. 5 is an end view of the fluid coupling device of FIG. 1.
Figure 6:
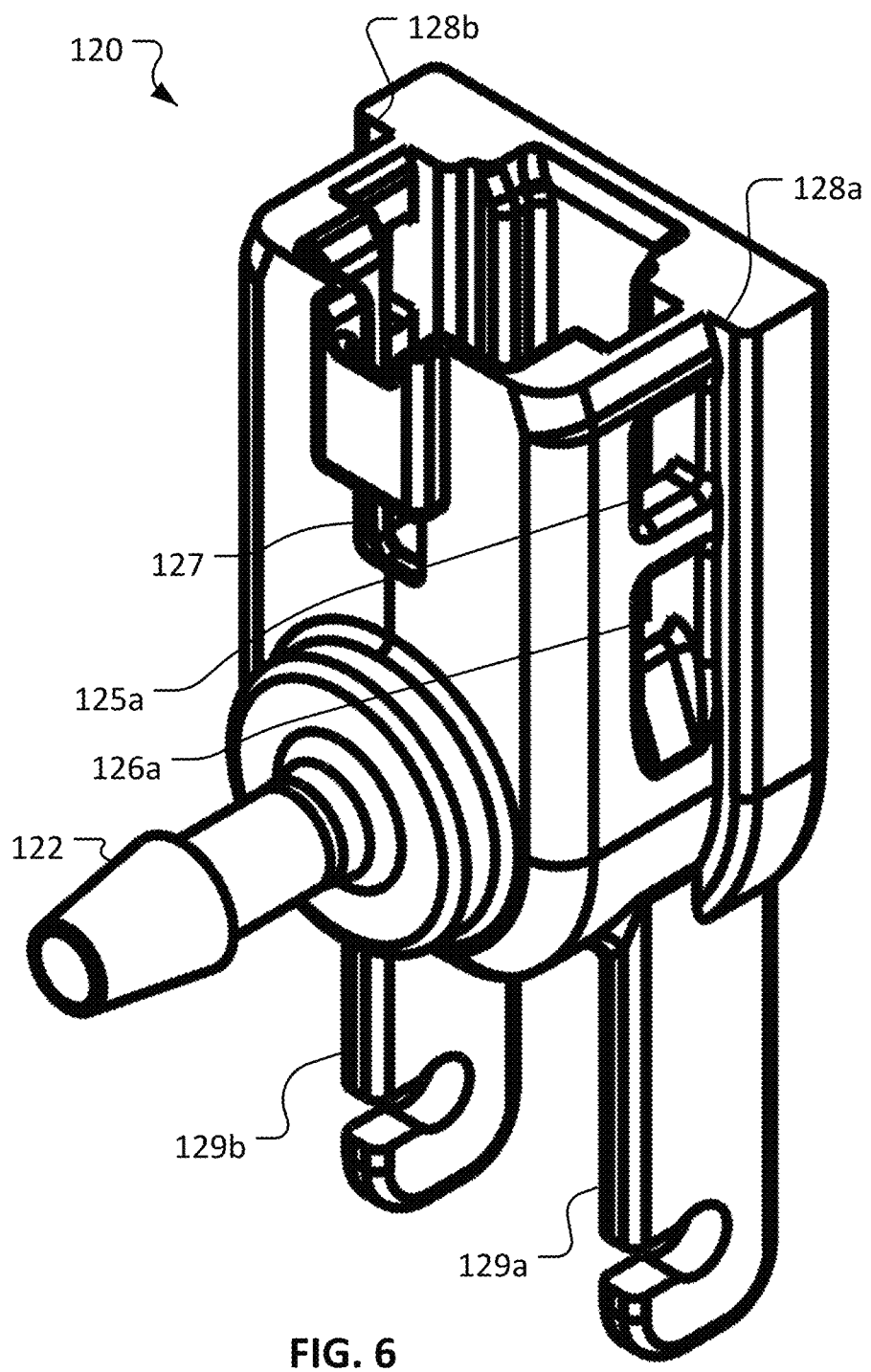
FIG. 6 is a perspective view of a body of the fluid coupling device of FIG. 1.
Figure 7:
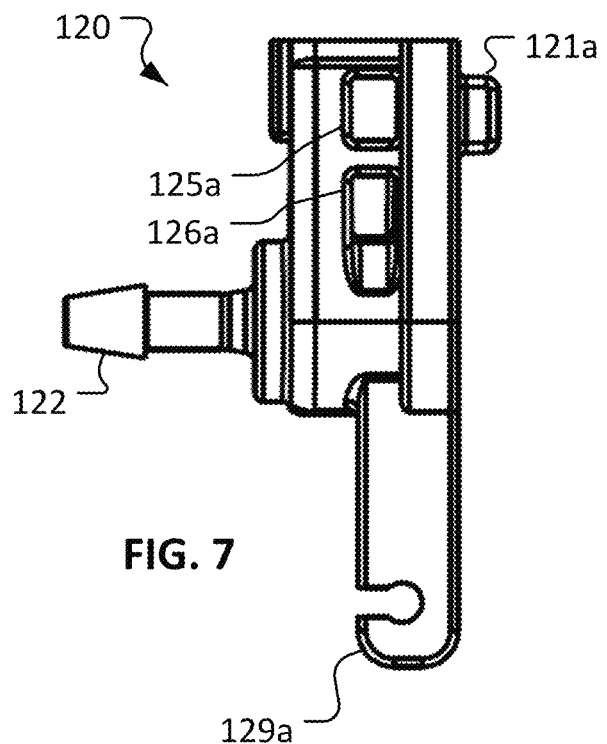
FIG. 7 is a side view of the body of FIG. 6.

Referring to FIG. 1, some example embodiments of a fluid system 10 include one or more example fluid coupling devices 100 configured to, for example, releasably connect a first fluid system equipment or container 20 to a second fluid system equipment or container 30. In some implementations, the fluid system 10 may include at least one fluid coupling device 100 that is a single-use, aseptic disconnection fluid coupling device, in which a first coupling 110 and second coupling 110 are configured to be disconnected from one another in a manner that provides a non-spill aseptic disconnection, and that mechanically prevents reconnection to each other or other couplings, and prevents reuse of the fluid path through the first coupling 110 and second coupling 110. (The first coupling 110 and the second coupling 110 are sometimes collectively referred to herein as "couplings," "coupling halves," or singularly referred to as a "coupling-half")

In one non-limiting example, the fluid coupling device 100 can provide a single-use, aseptic disconnection capability for the fluid flow path between the fluid system equipment 20 in the form of a bioreactor system (connected directly to the fluid coupling device 100 or connected via a fluid tube 22) and the fluid system container 30, sometimes in the form of a media bag (connected directly to the fluid coupling device 100 or connected via a fluid tube 32).

The fluid coupling device 100 can be provided to the end user in the coupled, operative configuration as shown. In the coupled, operative configuration the fluid coupling device 100 provides an open fluid flow path through the fluid coupling device 100 from a first termination 122 to a second termination 122. Then, after use as desired, the fluid coupling device 100 can be reconfigured to separate the first coupling 110 from the second coupling 110. In the separated configuration, the fluid flow paths through the first coupling 110 and the second coupling 110 are closed. In other words, the process for uncoupling the first coupling 110 from the second coupling 110 also causes the fluid flow paths through the first coupling 110 and the second coupling 110 to become closed, as described further below.

In some cases, the fluid coupling device 100 is provided to the end user in a sterile condition, or is made to be compatible with sterilization. As used herein, the term "sterilize" means a process of freeing, to a specified degree, a surface or volume from microorganisms. In example embodiments, the sterility of various components can be achieved using one or more sterilization techniques, including gamma irradiation, E-beam, ethylene oxide (EtO), and/or autoclave technologies. In some cases, the fluid coupling device 100 is provided to the end user as a component of a system.

Referring also to FIGS. 2-5, in some embodiments (such as the depicted embodiment), the first coupling 110 and second coupling 110 are identical or substantially identical. Accordingly, the first coupling 110 and second coupling 110 can be considered to be genderless couplings (e.g., substantially identical except for possibly differences in the styles of the terminations 122). In the context of this disclosure, "genderless" means that the coupling halves are substantially similar in that there are no particular male couplings and female couplings. However, in some embodiments of the fluid coupling device 100 the first coupling 110 and second coupling 110 are structurally different from each other, as desired.

Typically, the fluid coupling device 100 is provided to an end user in the operative, coupled arrangement (as depicted). In the operative, coupled configuration (also referred to herein as the first configuration) the mated first coupling 110 and second coupling 110 define an open, two-way fluid flow path 101 that extends along a longitudinal axis 102.

The fluid coupling device 100 includes a removable retainer 130 partially surrounding the mated first coupling 110 and second coupling 110. The removable retainer 130 mechanically constrains the first coupling 110 and second coupling 110 to be abutting against each other in the operative, coupled configuration. When the removable retainer 130 is uncoupled from the mated first coupling 110 and second coupling 110, the first coupling 110 and second coupling 110 can then be separated from each other and the fluid flow path 101 will be blocked, as described further below.

In the fully coupled, operable configuration as shown, fluid can flow through the fluid coupling device 100 between a first termination 122 of the first coupling 110 and a second termination 122 of the second coupling 110. While the terminations are depicted as barbed connections, it should be understood that the couplings 110 can have any type of terminations/connections such as, but not limited to, threaded connections, elbows, tees, sanitary fittings, Y-fittings, compression fittings, any type of adapter, and the like, and combinations thereof.

The materials from which one or more of the components of the fluid coupling device 100 are made of include thermoplastics. In particular embodiments, the materials from which the components of the fluid coupling device 100 are made of are thermoplastics, such as, but not limited to, acetal, ABS, polycarbonate, polysulfone, polyether ether ketone, polysulphide, polyester, polyvinylidene fluoride (PVDF), polyethylene, polyphenylsulfone (PPSU; e.g., Radel®), polyetherimide (PEI; e.g., Ultem®), polypropylene, polyphenylene, polyaryletherketone, and the like, and combinations thereof.

In some embodiments, the materials from which one or more of the components of the fluid coupling device 100 are made of include metals such as, but not limited to stainless steel, brass, aluminum, plated steel, and the like. In particular embodiments, the fluid coupling device 100 is metallic-free.

Each of the couplings 110 includes a body 120, a seal 140, a cover 150, and a closure clip 160. The body 120 includes termination 122. The seal 140 is disposed within a seal recess 123 defined by the body 120, as described further below. The cover 150 is movably coupled (e.g., pivotably coupled) to the body 120. The closure clip 160 is movably coupled to the body 120.

Figure 10:
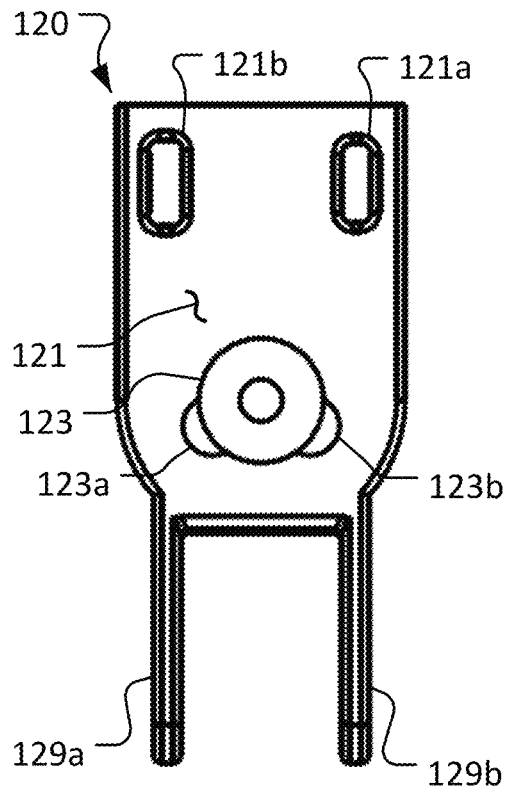
FIG. 10 is a first end view of the body of FIG. 6.
Figure 11:
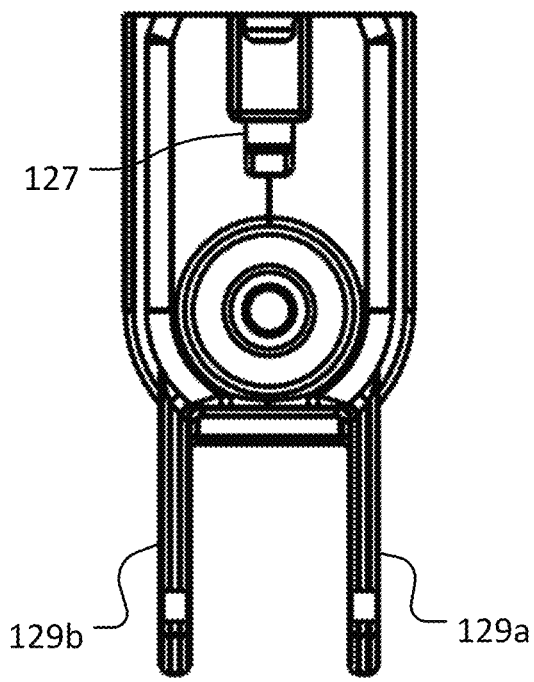
FIG. 11 is a second end view of the body of FIG. 6.

FIGS. 6-11 illustrate various views of the body 120. The body 120 includes a front face 121 (FIG. 10). The front faces 121 of each of the couplings 110 are abutted against each other when the fluid coupling device 100 is in the operative, coupled configuration (e.g., see FIG. 3).

A projection 121a extends from the front face 121. The front face 121 also defines a recess 121b that is sized and shaped to releasably receive the projection 121a. That is, when the fluid coupling device 100 is in the coupled, operative configuration, the projection 121a of the first coupling 110 is disposed within the recess 121b of the second coupling 110, and the projection 121a of the second coupling 110 is disposed within the recess 121b of the first coupling 110.

The body 120 also defines a seal recess 123. The seal recess 123 is open to the front face 121. The shape of the seal recess 123 is cylindrical with two open side adjuncts 123a and 123b. The side adjuncts 123a-b provide spaces for the seal 140 to be deformed into when the seal 140 is compressed by the closure clip 160 (as described further below).

Figure 8:
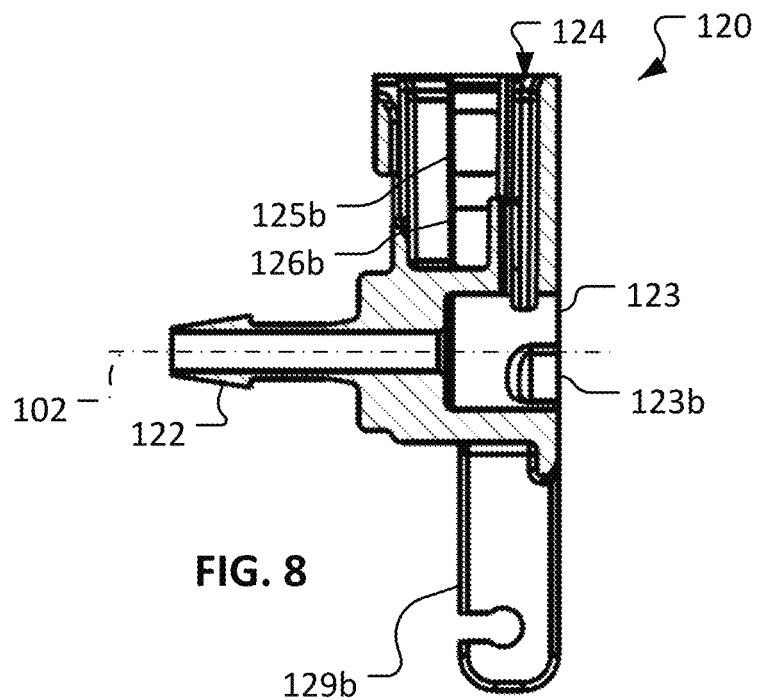
FIG. 8 is a longitudinal cross-sectional view of the body of FIG. 6.
Figure 9:
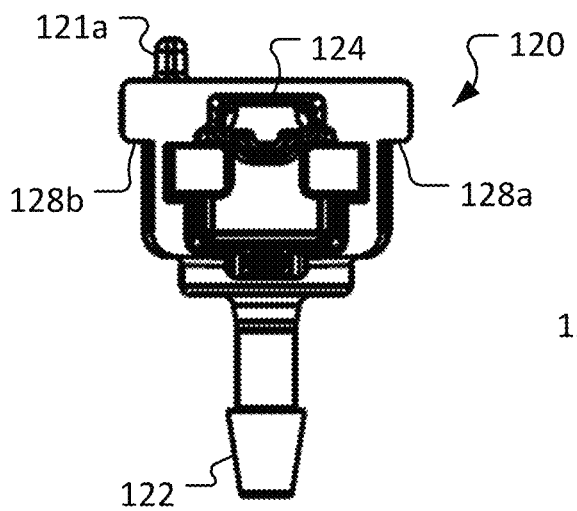
FIG. 9 is a top view of the body of FIG. 6.

The body 120 defines a lateral passageway 124 that extends into the seal recess 123 (e.g., see FIG. 8). The lateral passageway 124 slidably receives a projection 161 of the closure clip 160 (see FIGS. 20-23). Accordingly, when the closure clip 160 is pressed into the body 120, the projection 161 laterally compresses the seal 140 within the seal recess 123 (see FIG. 28). That results in blockage of the fluid flow through the coupling 110. The lateral passageway 124 helps direct and support the projection 161 so that it compresses the seal 140 properly, and without buckling or misalignment.

The body 120 also defines first lateral openings 125a and 125b, and second lateral openings 126a, and 126b. The first lateral openings 125a and 125b are laterally opposite of each other, and the second lateral openings 126a and 126b are laterally opposite of each other. The second lateral openings 126a-b are closer to the flow path axis 102 than the first lateral openings 125a-b are. As described further below, the first lateral openings 125a-b releasably receive lateral barbs 132a-b of the retainer 130 (FIGS. 12-14) and the lateral barbs 162a-b of the closure clip 160 (FIGS. 20 and 21) while the fluid coupling 100 is in the operative, coupled configuration as shown in FIGS. 1-5. Then, when the closure clip 160 is pressed into the body 120, the lateral barbs 162a-b of the closure clip 160 move from the first lateral openings 125a-b and snap into irreversible latched engagement the second lateral openings 126a-b. Pressing the closure clip 160 into the body 120 also disengages the lateral barbs 132a-b of the retainer 130 from the lateral openings 125a-b so that the retainer 130 can be removed from the couplings 110.

The body 120 also defines an end opening 127. The end opening 127 releasably receives an end barb 163 of the closure clip 160 (FIGS. 22 and 23) when the closure clip 160 is pressed into the body 120 in preparation for disconnecting the couplings 110 from each other. That is, when the closure clip 160 is pressed into the body 120, the end barb 163 snaps into the end opening 127 and thereby retains the closure clip 160 in the compressed orientation relative to the body 120. The end opening 127 also serves as a window that facilitates a visual indication of when the end barb 163 is in the end opening 127, which indicates that the closure clip 160 is latched in its compressed orientation relative to the body 120.

Figure 12:
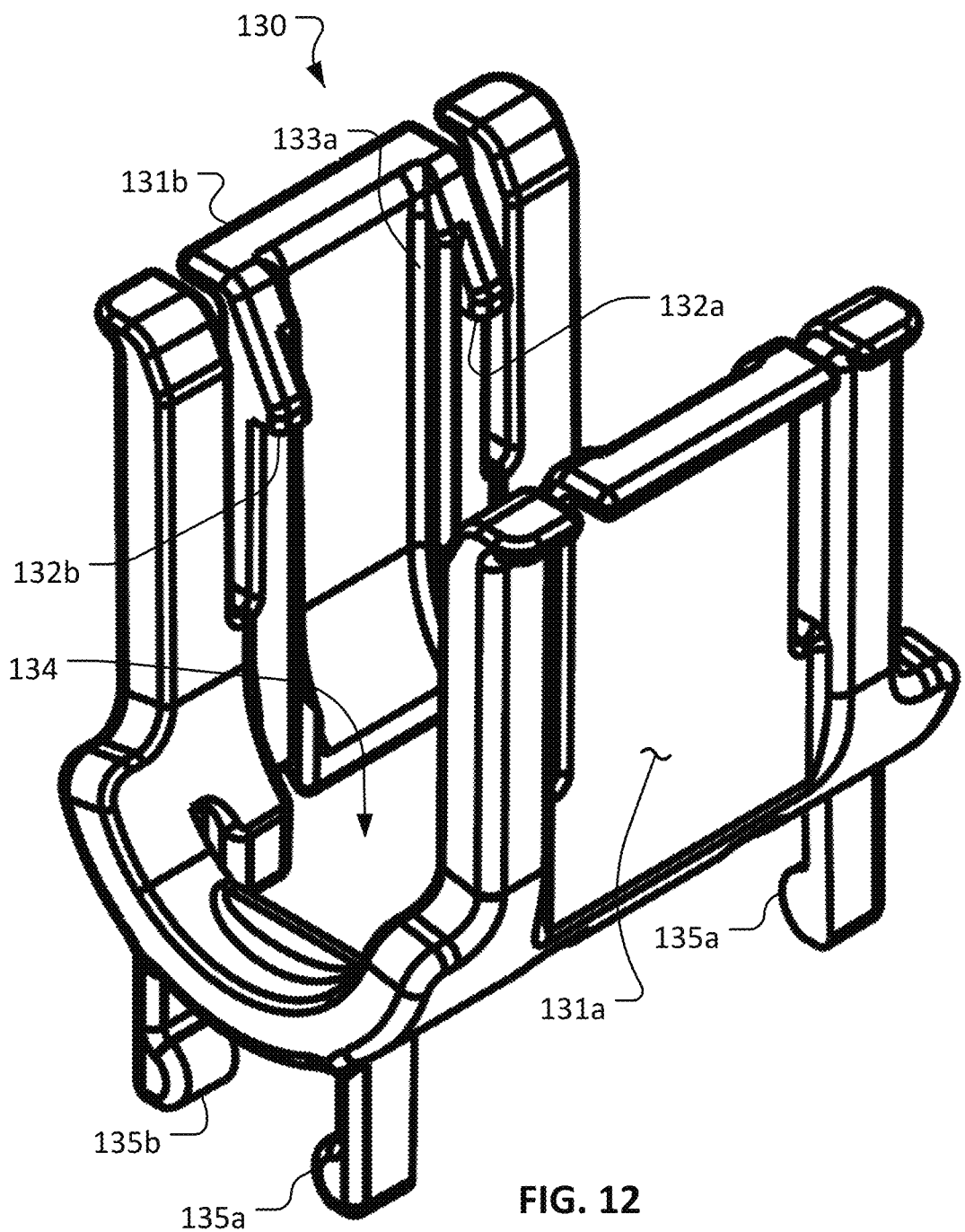
FIG. 12 is a perspective view of a retainer of the fluid coupling device of FIG. 1.
Figure 13:
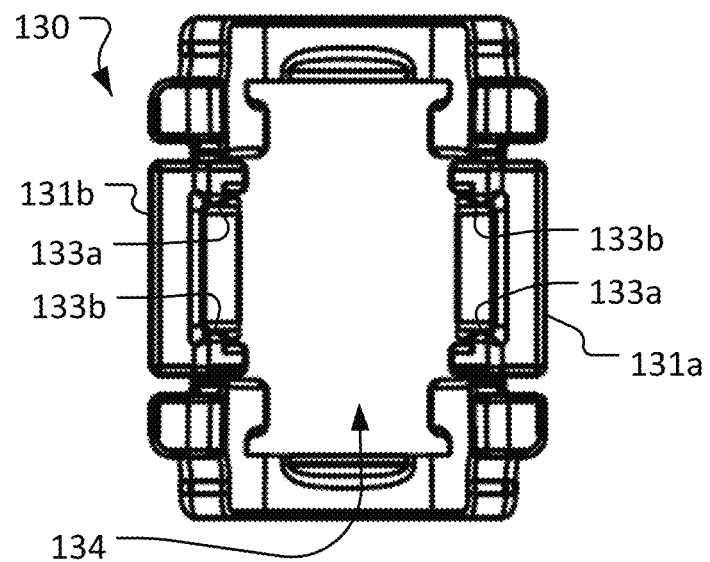
FIG. 13 is a top view of the retainer of FIG. 12.

The body 120 also includes side flanges 128a and 128b. The side flanges 128a-b are slidably engaged with clamp surfaces 133a-b of the retainer 130 (FIGS. 12 and 13). The engagement between the clamp surfaces 133a-b of the retainer 130 and the side flanges 128a-b of the body 120 compresses and retains the two couplings 110 against each other as shown in FIGS. 1-5.

The body 120 also includes arms 129a and 129b. The covers 150 (FIGS. 18 and 19) are pivotably coupled to the arms 129a-b of the body 120.

Figure 14:
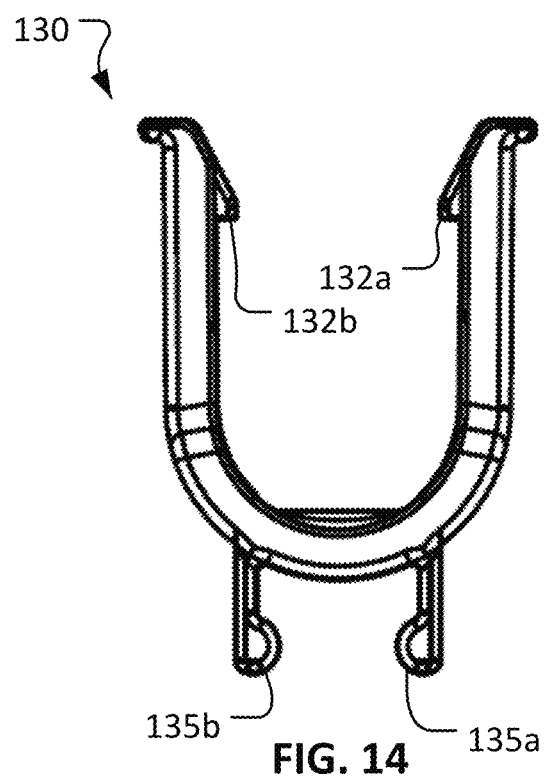
FIG. 14 is an end view of the retainer of FIG. 12.

FIGS. 12-14 illustrate various views of the retainer 130. The retainer 130 has a U-shaped cross-section and defines a mid-body bottom opening 134. The retainer 130 includes mid-body sidewalls 131a and 131b. The lateral barbs 132a-b project laterally inward from each of the mid-body sidewalls 131a and 131b. That is, a pair of the lateral barbs 132a-b projects laterally inward from the mid-body sidewall 131a, and another pair of the lateral barbs 132a-b projects laterally inward from the mid-body sidewall 131b. The lateral barbs 132a-b are engaged in the first lateral openings 125a-b of the bodies 120 of the couplings 110 when the fluid coupling device 100 is in the operative, coupled configuration (FIGS. 1-5). The engagement between the lateral barbs 132a-b and the first lateral openings 125a-b mechanically latches the retainer 130 on the couplings 110.

The mid-body sidewalls 131a-b are configured to elastically bend, deflect, or flex laterally outward when the closure clips 160 are compressed into the body 120. That is, the closure clips 160 include wedges 164a-b (e.g., FIGS. 20 and 21) that progressively force the mid-body sidewalls 131a-b laterally outward as the closure clips 160 are being compressed into the body 120. When the mid-body sidewalls 131a-b elastically bend, deflect, or flex laterally outward from the forces exerted by the wedges 164a-b, then the lateral barbs 132a-b become unengaged from the first lateral openings 125a-b of the bodies 120. When the lateral barbs 132a-b become unengaged from the first lateral openings 125a-b of the bodies 120, then the retainer 130 can be removed from the couplings 110.

The retainer 130 includes engagement surfaces 133a and 133b (FIG. 13). The engagement surfaces 133a-b abut against the side flanges 128a-b of the couplings 110 to compress the couplings 110 together (front face 121 to front face 121). In addition to the abutment of the front faces 121 of the body 120, front faces of the seals 140 are also compressed against each other (to form a fluid-tight seal therebetween).

The retainer 130 also includes cover latch members 135a and 135b. The cover latch members 135a-b can releasably engage with the covers 150 to maintain the positions of the covers 150 in arrangements depicted in FIGS. 1-5. A user can unlatch the covers 150 from the cover latch members 135a-b by manually unsnapping the covers 150 from the cover latch members 135a-b.

Figure 15:
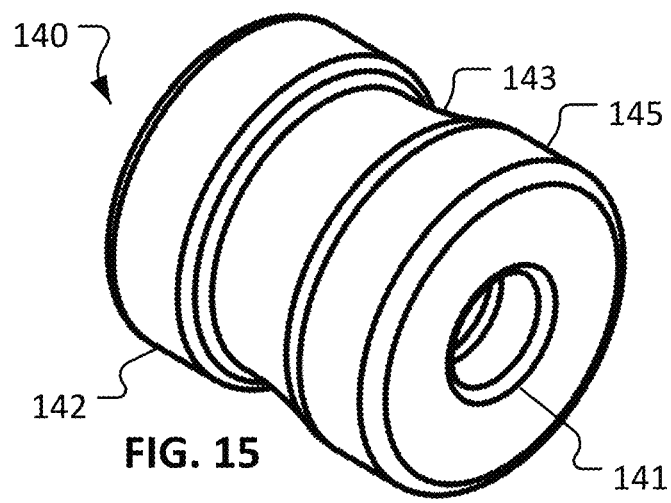
FIG. 15 is a perspective view of a seal of the fluid coupling device of FIG. 1.
Figure 16:
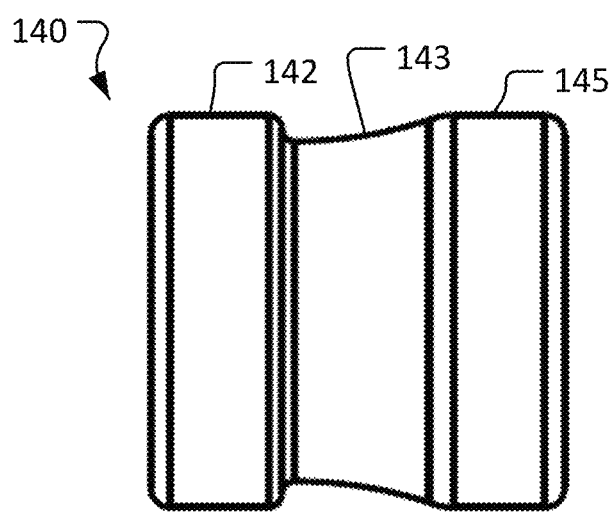
FIG. 16 is a side view of the seal of FIG. 15.
Figure 17:
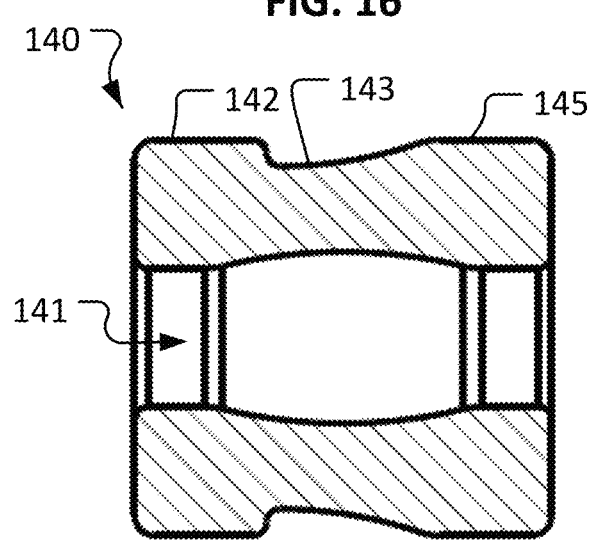
FIG. 17 is a longitudinal cross-sectional view of the seal of FIG. 15.

FIGS. 15-17 illustrate various views of the seal 140. In certain embodiments, seals 140 of the fluid coupling device 100 can be made of materials such as, but not limited to, silicone, fluoroelastomers (FKM), ethylene propylene diene monomer (EPDM), thermoplastic elastomers (TPE), buna, buna-N, thermoplastic vulcanizates (TPV), and the like. In some embodiments, the seal 140 has a cross-sectional shape that is an hourglass-shape, an oval shape, a circular shape, a polygonal shape, a multi-lobe shape, or any other suitable shape.

This seal 140 (while shown here in isolation) is positioned in the seal recess 123 defined by the body 120 (e.g., FIGS. 8 and 10) such that an end portion of the seal 140 (or front face portion) protrudes slightly from the front face 121 of the body 140. Accordingly, when the front faces 121 of two couplings 110 are abutted against each other, the front faces of the seals 140 contact each other and the seals 140 become longitudinally compressed to create a fluid-tight seal.

In the depicted embodiment, the seal 140 defines a central longitudinal bore 141. The outer diameter of the seal 140 includes a first cylindrical end portion 142, a second cylindrical end portion 145, and a waist portion 143 between the end portions 142 and 145. The outer diameter of the waist portion 143 is smaller than the outer diameters of the end portions 142 and 145. In some embodiments, the waist portion 143 is frustoconical in shape. In some embodiments, such as the depicted embodiment, the waist portion 143 has an outer profile that is curved (e.g., arcuate) rather than linear.

The bore 141 comprises two cylindrical end portions and a central portion (between the cylindrical end portions) that is a segment of an ovoid (with its ends truncated). In embodiments having an arcuate outer profile of the waist portion 143, the center of the arc of the outer profile of the waist portion 143 is located in an opposite direction in comparison to the center of the arc of the internal central portion. In some such embodiments, the radii of the arcuate outer profile of the waist portion 143 and the arc of the internal central portion are unequal. In some such embodiments, the radii of the arcuate outer profile of the waist portion 143 and the arc of the internal central portion are equal.

Figure 18:
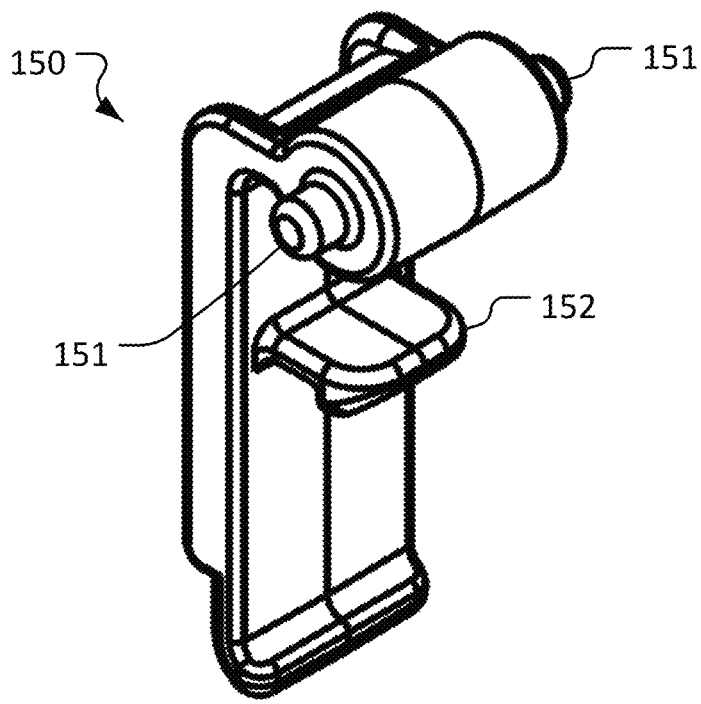
FIG. 18 is a perspective view of a cover of the fluid coupling device of FIG. 1.
Figure 19:
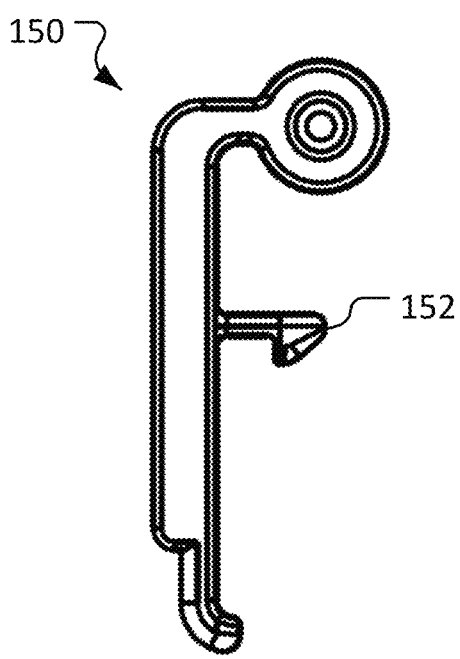
FIG. 19 is a side view of the cover of FIG. 18.
Figure 20:
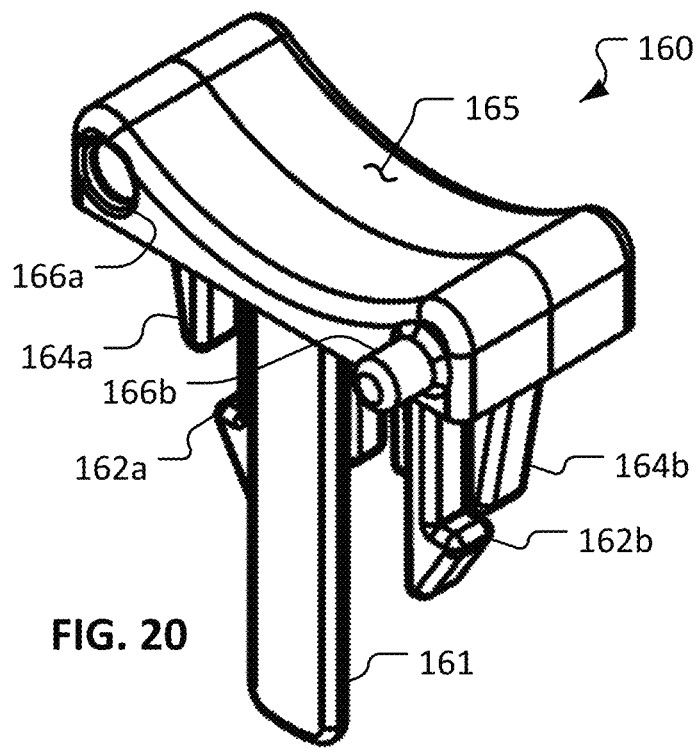
FIG. 20 is a perspective view of a closure clip of the fluid coupling device of FIG. 1.
Figure 21:
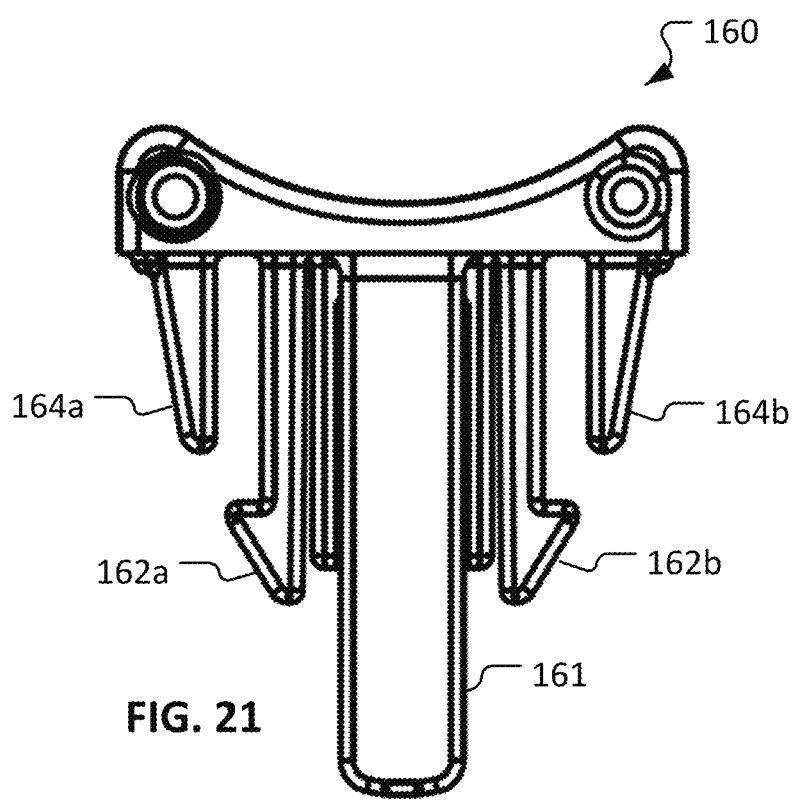
FIG. 21 is an end view of the closure clip of FIG. 20.
Figure 22:
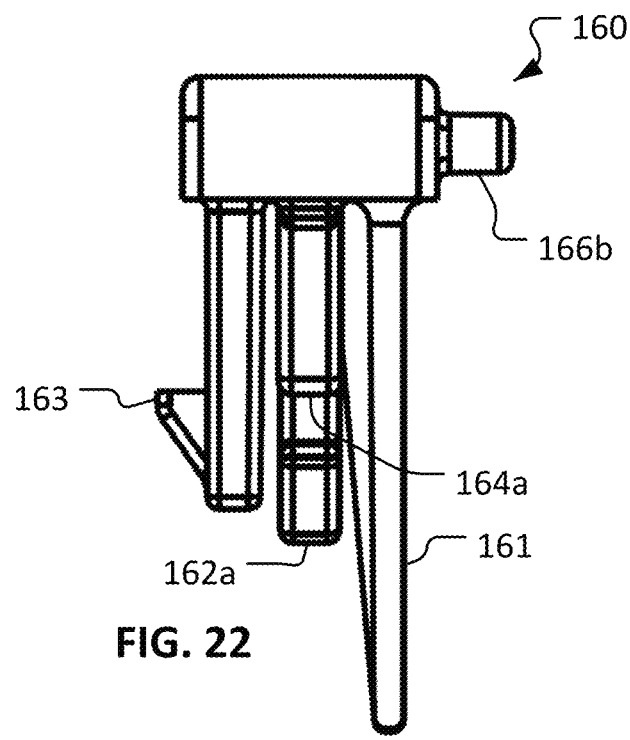
FIG. 22 is a side view of the closure clip of FIG. 20.
Figure 23:
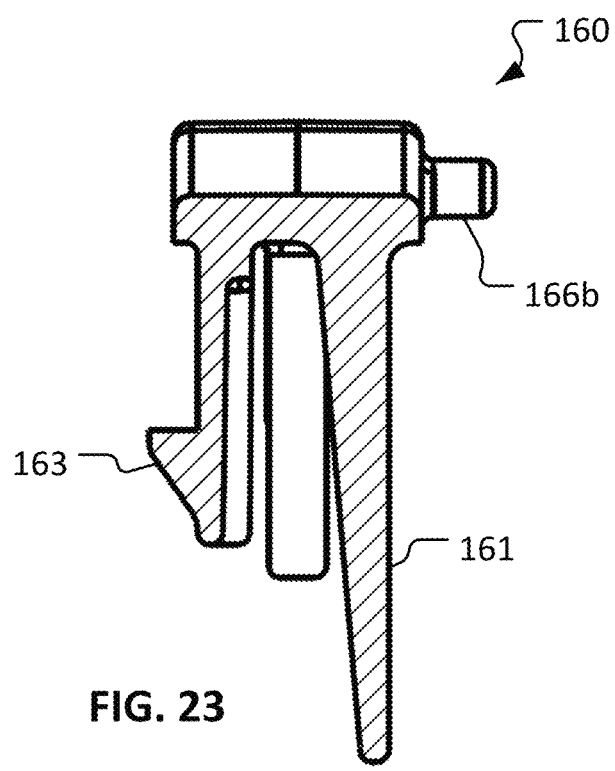
FIG. 23 is a longitudinal cross-sectional view of the closure clip of FIG. 20.
Figure 24:
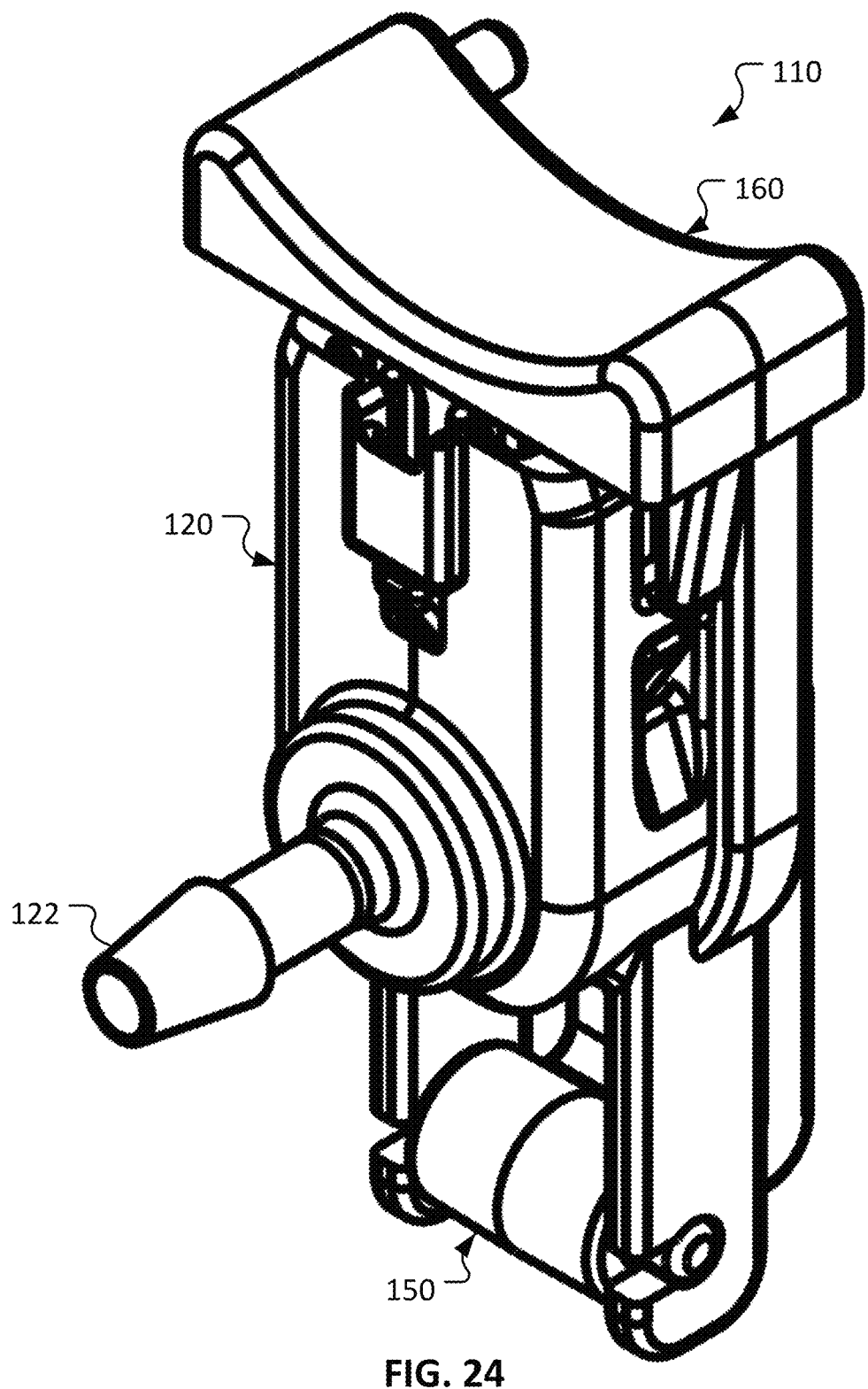
FIG. 24 is a perspective view of a single coupling of the fluid coupling device of FIG. 1.
Figure 25:
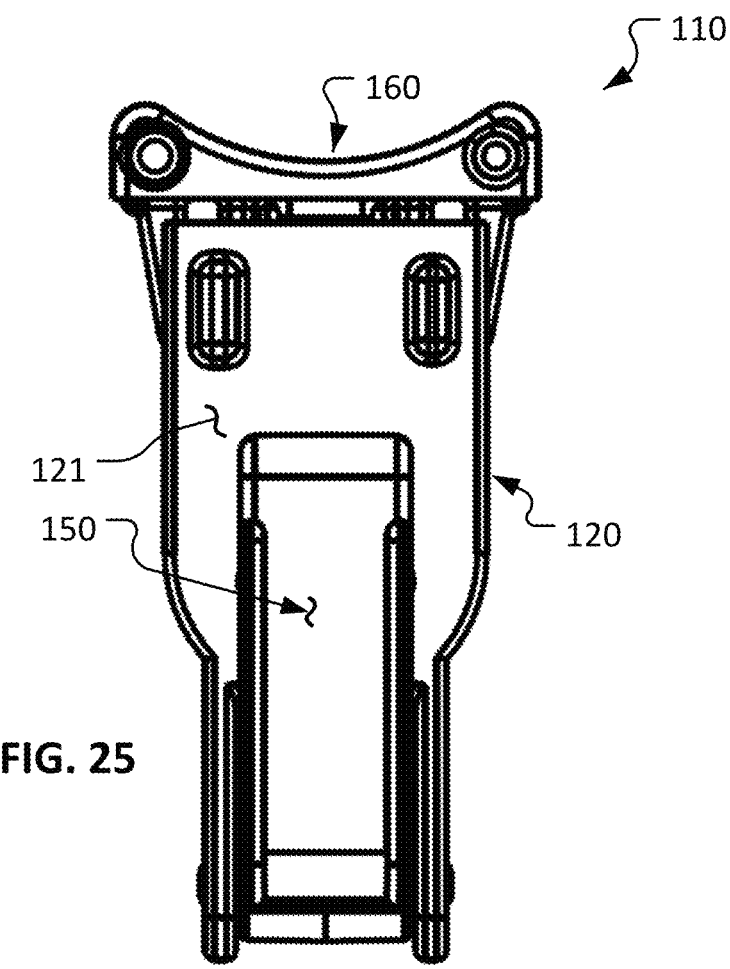
FIG. 25 is an end view of the single coupling of FIG. 24.
Figure 26:
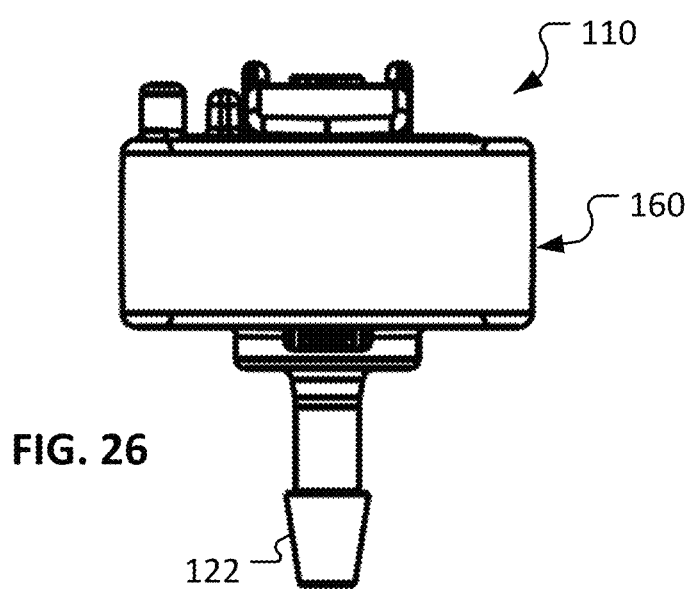
FIG. 26 is a top view of the single coupling of FIG. 24.
Figure 27:
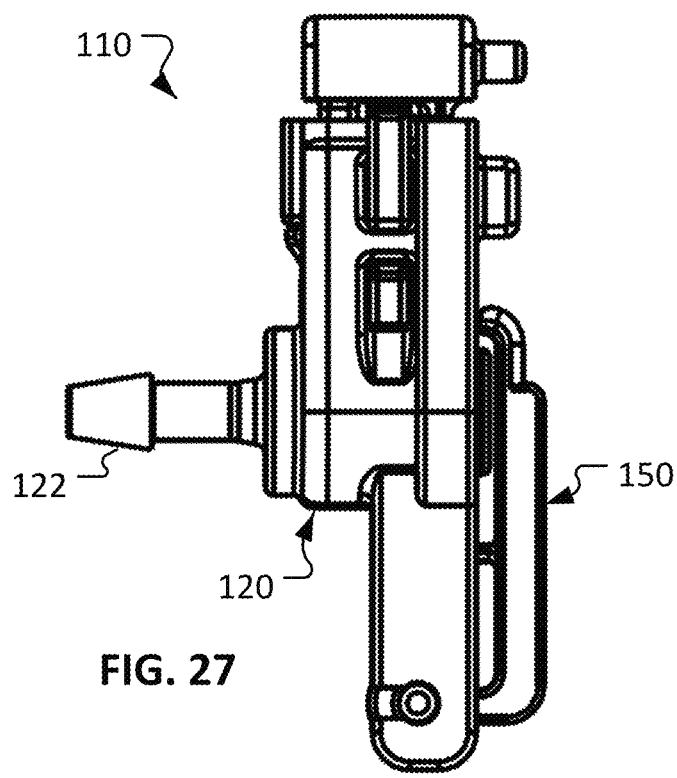
FIG. 27 is a side view of the single coupling of FIG. 24.

FIGS. 18 and 19 illustrate various views of the cover 150. It should be understood that the cover 150 is an optional component. Some embodiments of the coupling 110 do not include a cover 150.

Figure 28:
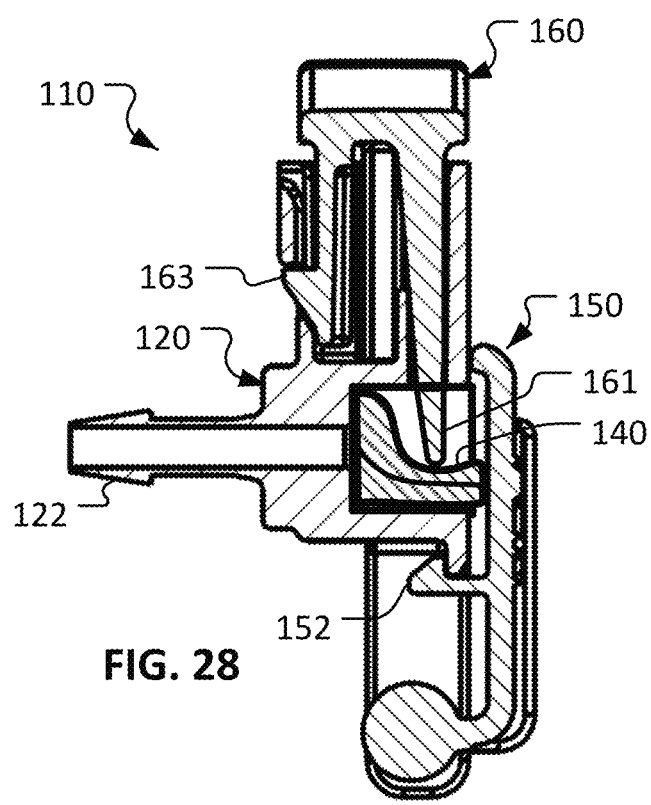
FIG. 28 is a longitudinal cross-sectional view of the single coupling of FIG. 24.
Figure 29:
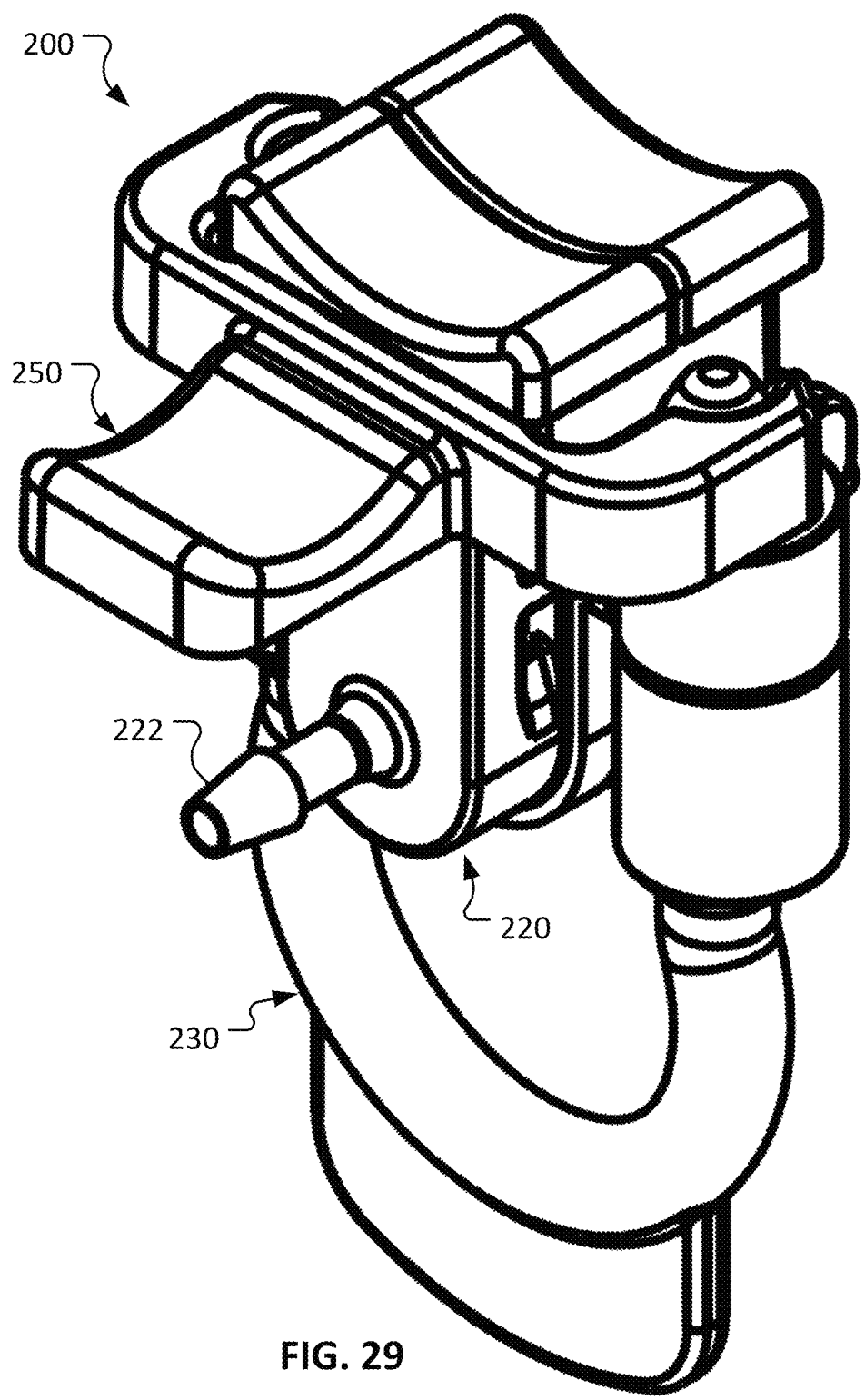
FIG. 29 is a perspective view of another example fluid coupling device in accordance with some embodiments described herein.
Figure 30:
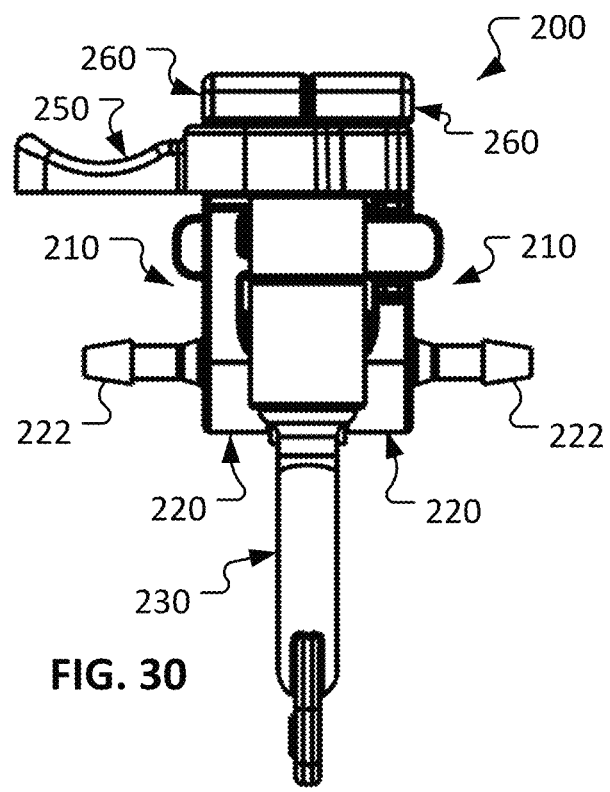
FIG. 30 is a side view of the fluid coupling device of FIG. 29.
Figure 31:
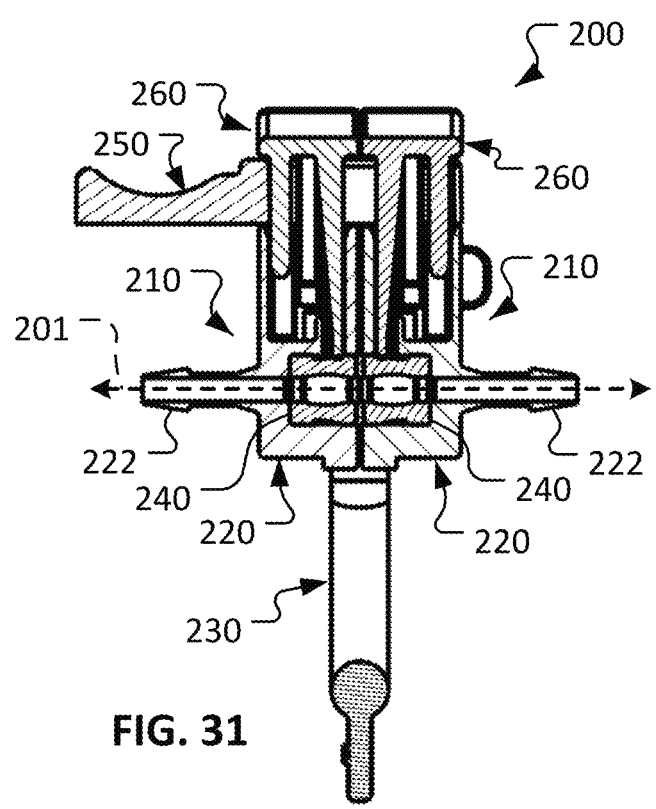
FIG. 31 is a longitudinal cross-sectional view of the fluid coupling device of FIG. 29.
Figure 32:
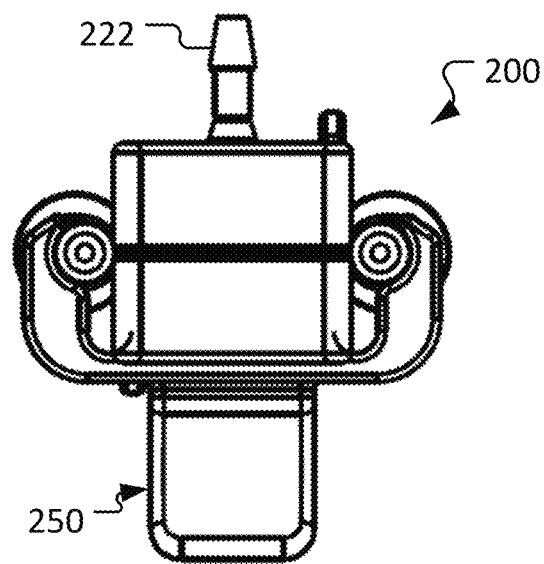
FIG. 32 is a top view of the fluid coupling device of FIG. 29.
Figure 33:
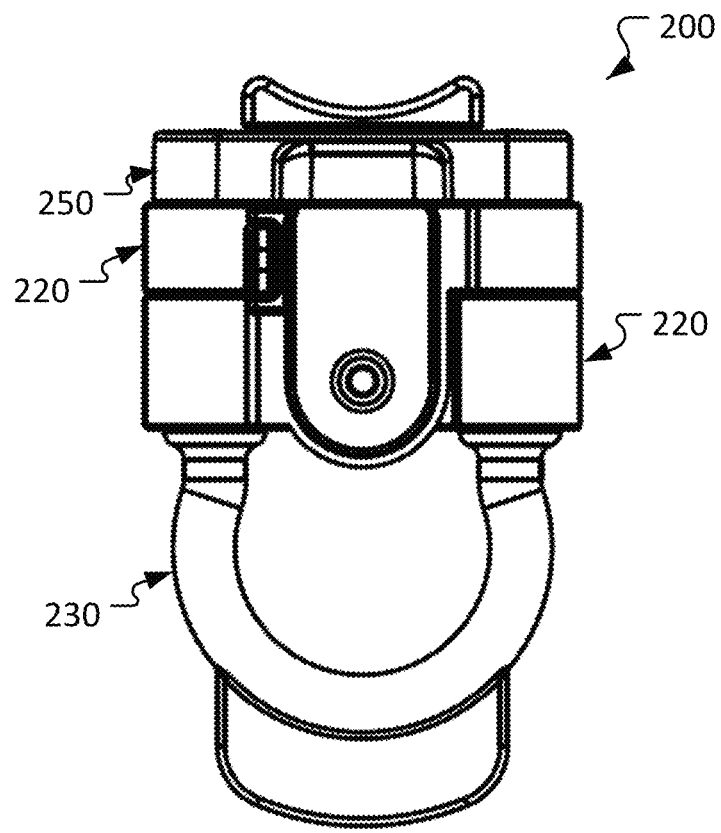
FIG. 33 is an end view of the fluid coupling device of FIG. 29.
Figure 34:
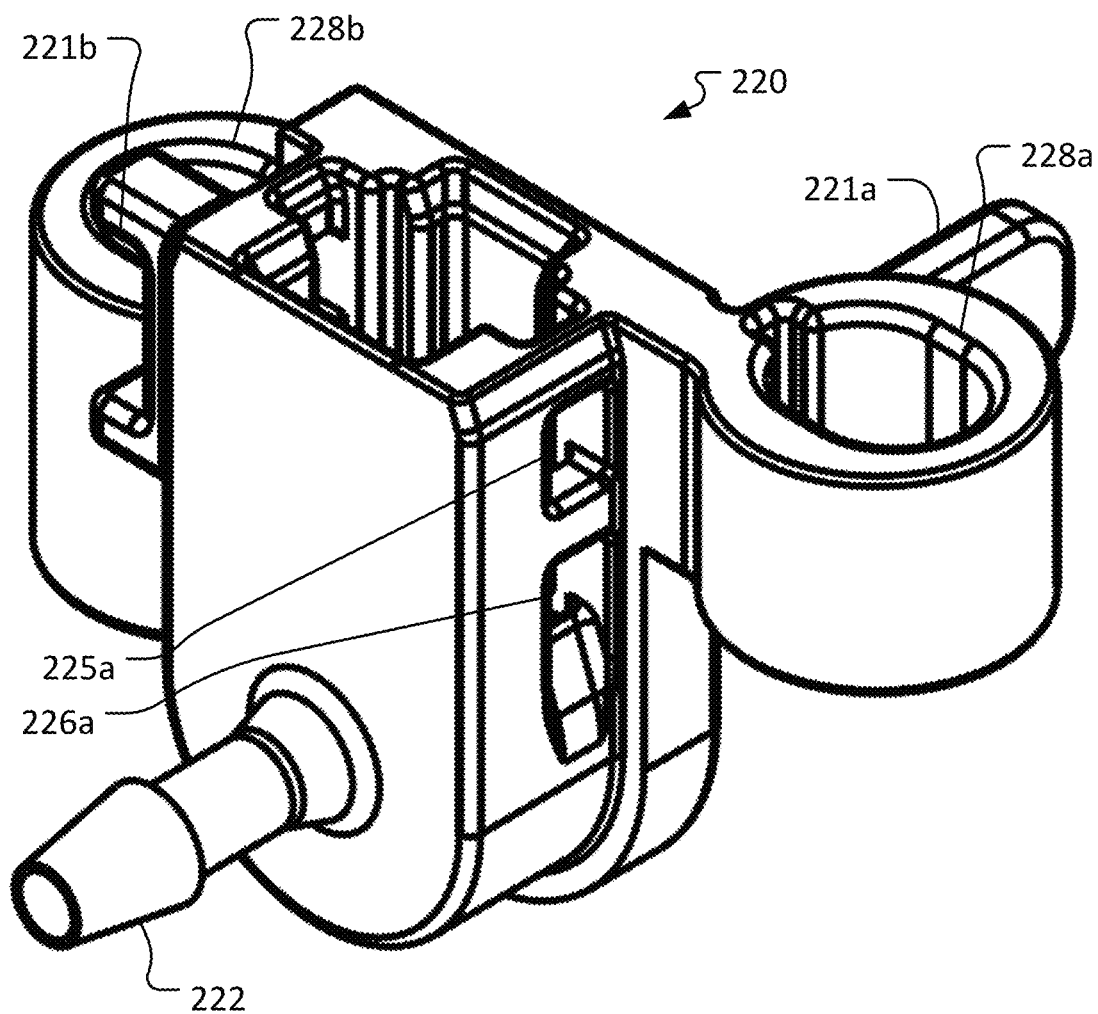
FIG. 34 is a perspective view of a body of the fluid coupling device of FIG. 29.
Figure 35:
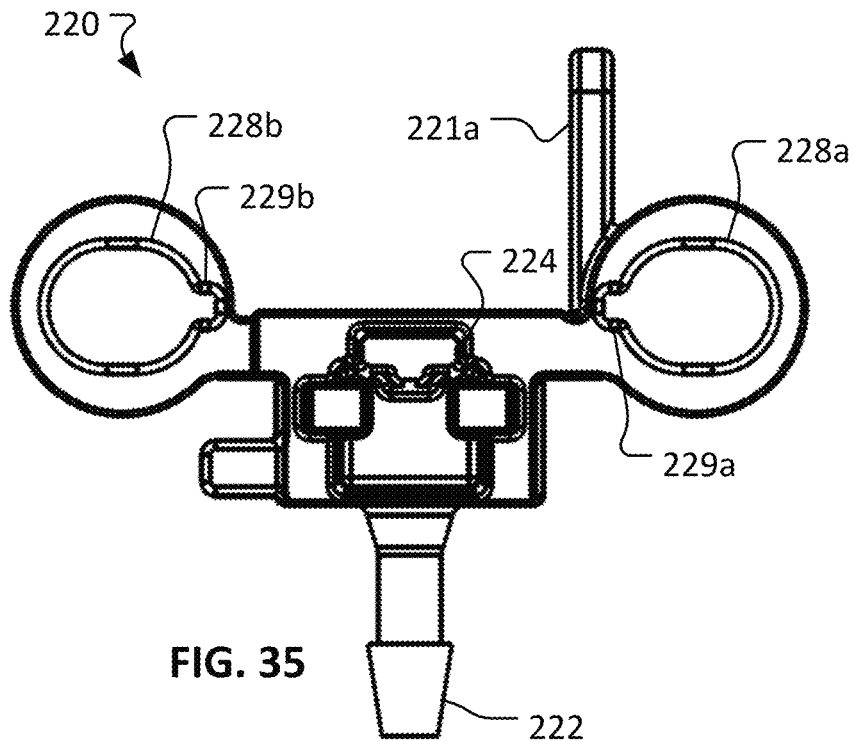
FIG. 35 is a top view of the body of FIG. 34.
Figure 36:
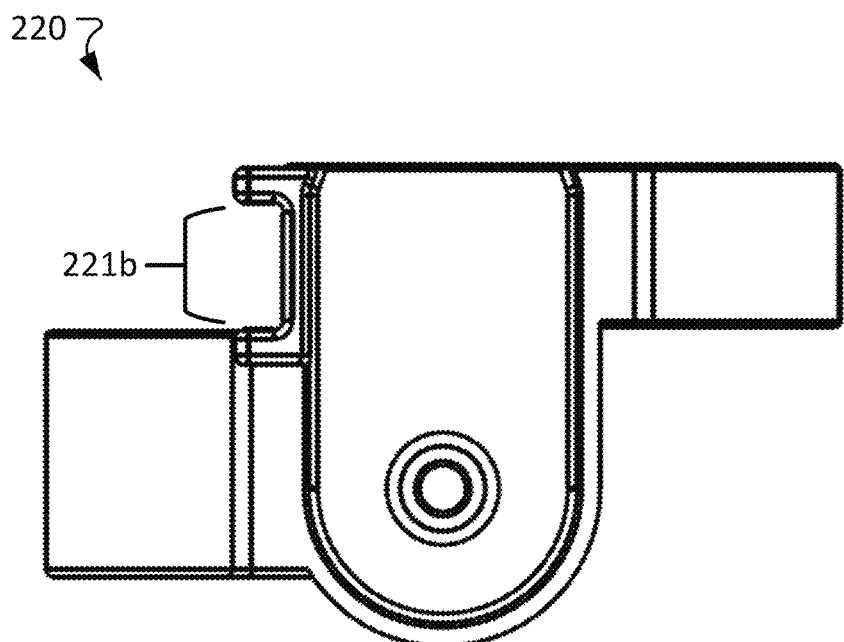
FIG. 36 is an end view of the body of FIG. 34.
Figure 37:
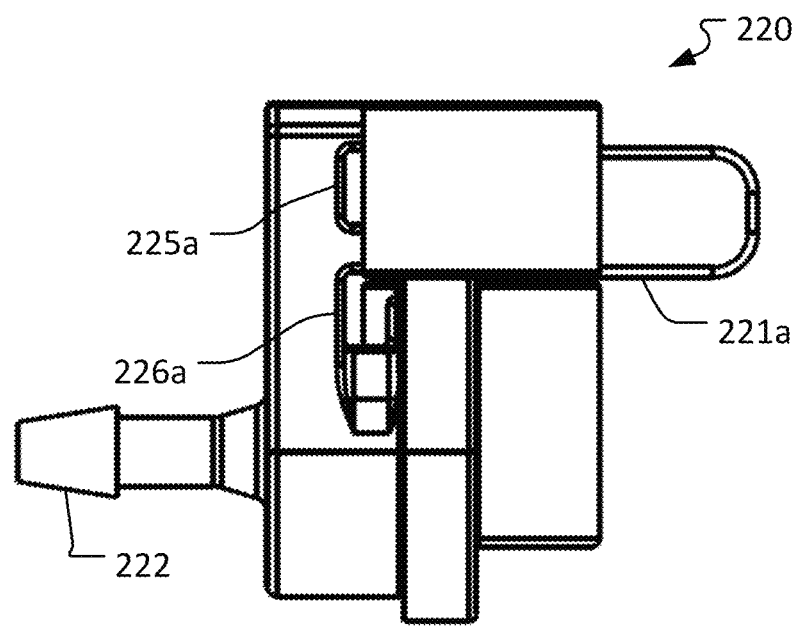
FIG. 37 is a side view of the body of FIG. 34.
Figure 38:
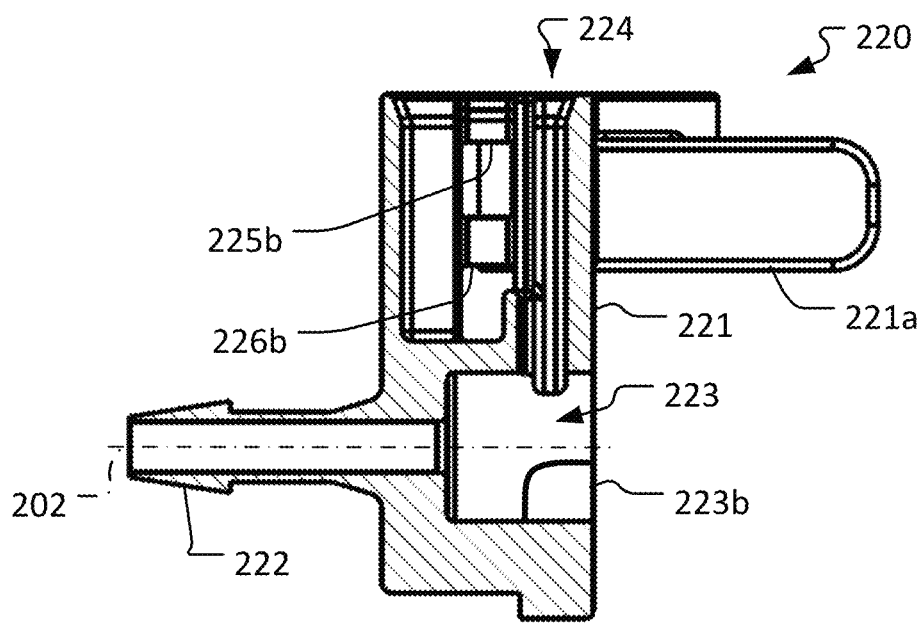
FIG. 38 is a longitudinal cross-sectional view of the body of FIG. 34.

The cover 150 includes two pins 151 by which the cover 150 is pivotably coupled with the arms 129a-b of the body 120. The cover 150 also includes a barb 152 that latches to the body 120 (as shown in FIG. 28). The design of the barb 152 prevents the cover 150 from being unlatched from the body 120 once the barb 152 has fully engaged (e.g., snapped into engagement) with the body 120.

FIGS. 20-23 illustrate various views of the closure clip 160. The closure clip 160 is movably coupled to the body 120. That is, the closure clip 160 can be depressed farther into the body 120 along a path that is perpendicular to the longitudinal axis 102 of the flow path 101 that extends through the body 120 (and through the bore 141 of the seal 140). The closure clip 160 includes the projection 161. The projection 161 compresses the seal 140 when the closure clip 160 is depressed into the body 120 (as shown in FIG. 28, for example). The compression of the seal 140 results in a closure of the flow path 101.

The closure clip 160 also includes the lateral barbs 162*a-b*. The lateral barbs 162*a-b* are engaged in the first lateral openings 125*a-b* of the body 120 when the fluid coupling device is in the operative, coupled configuration as shown in FIGS. 1-5. Then, when the closure clip 160 is depressed into the body 120, the lateral barbs 162*a-b* become unengaged from the first lateral openings 125*a-b* and snap into locked engagement with the second lateral openings 126*a-b*.

The closure clip 160 also includes the end barb 163. When the closure clip 160 is depressed into the body 120, the end barb 163 snaps into locked engagement with the end opening 127 defined by the body 120. A visual indication of the locked engagement is provided because the end barb 163 is visible in the end opening 127.

The closure clip 160 also includes the wedges 164*a-b*. When the closure clip 160 is depressed into the body 120, the wedges 164*a-b* slide along the lateral barbs 132*a-b* of the retainer 130 and cause a deflection of the mid-body sidewalls 131*a-b* so that the lateral barbs 132*a-b* disengage from the first lateral openings 125*a-b* of the body 120, so that the retainer 130 can be removed from the couplings 110.

The closure clip 160 also includes a concave thumb pad surface 165. A user can comfortably apply pressure to the thumb pad surface 165 to depress the closure clip 160 into the body 120 when disconnection of the couplings 110 is desired.

The closure clip 160 also includes a recess 166*a* and a projection 166*b*. The projection 166*b* is sized and shaped to be releasably received in the recess 166*a*. When the fluid coupling device 100 is in the operative, coupled configuration (as shown in FIGS. 1-5), the closure clips 160 of the couplings 110 are adjacent to each other such that the projections 166*b* are engaged in the recesses 166*a* of the adjacent closure clips 160. This engagement releasably interlocks the adjacent closure clips 160 so that they move in unison when depressed into the bodies 120 by a user.

FIGS. 24-28 illustrate various view of a single coupling 110 after the fluid coupling device 100 has been reconfigured from the operative, coupled configuration shown in FIGS. 1-5 to an uncoupled configuration in which the retainer 130 has been removed and the two couplings 110 are separated from each other. To transition from the operative, coupled configuration to the uncoupled configuration the following steps are performed by a user. First, the closure clips 160 are depressed into the bodies 120. When the closure clips 160 are fully depressed, the closure clips 160 lock in the depressed orientation relative to the bodies 120 and the projections 161 compress and deform the seals 140 (as shown in FIG. 28, including deformation of the seals 140 into side adjuncts 123*a-b*) to fully close off the fluid flow paths through the couplings 110. Depressing the closure clips 160 also outwardly flexes the mid-body sidewalls 131*a-b* of the retainer 130 so that the retainer 130 is no longer latched onto the couplings 110.

Second, the covers 150 (when included) can be unlatched from the cover latch members 135*a-b* of the retainer 130. The covers 150 can then be pivoted toward each other and into alignment with the mid-body bottom opening 134 of the retainer 130.

Third, the retainer 130 can be pulled laterally off from the couplings 110. The retainer 130 can be discarded.

Fourth, the couplings 110 can be separated from each other.

Fifth, the covers 150 can be pivoted and latched to the bodies 120 as shown in FIGS. 24-28. In this orientation, the cover 150 can compress against the front face of the seal 140 while the seal 140 is also being compressed by the projection 161 of the closure clip 160. The covers 150, in combination with the lateral compression of the seal 140 by the projection 161, block the fluid flow path and help to prevent any spillage of fluid from the coupling 110.

FIGS. 29-33 illustrate another type of fluid coupling device 200 that has essentially the same operational features as the fluid coupling device 100 described above. However, this fluid coupling device 200 does not have any covers (such as the covers 150 described above), and this fluid coupling device 200 includes an optional removable spacer 250. The removable spacer 250 must be removed from engagement with the couplings 210 in order to be able to depress the closure clips 260.

The illustrated fluid coupling device 200 includes a first coupling 210, a second coupling 210, the retainer 230, and the optional spacer 250. Each of the couplings 210 includes a body 220, seal 240, and a closure clip 260. In some embodiments, the seal 240 and the closure clip 260 can be the same as the seal 140 and closure clip 160 described above. In some embodiments, the seal 240 and the closure clip 260 can be modified versions of the seal 140 and closure clip 160 described above.

An open, two-way fluid flow path 201 is defined through the fluid coupling device 200, between a termination 222 of the first coupling 210 and a termination 222 of the second coupling 210. The fluid flow path 201 extends through the bodies 220 and the bores of the seals 240.

In some embodiments (such as the depicted embodiment), the first coupling 210 and second coupling 210 are identical or substantially identical. Accordingly, the first coupling 210 and second coupling 210 can be considered to be genderless couplings (e.g., substantially identical except for possibly differences in the styles of the terminations 222). However, in some embodiments of the fluid coupling device 200 the first coupling 210 and second coupling 210 are structurally different from each other, as desired.

The fluid coupling device 200 can be provided to the end user in the coupled, operative configuration as shown. Then, after use as desired, the fluid coupling device 200 can be reconfigured to separate the first coupling 210 from the second coupling 210. In the separated configuration, the fluid flow paths through the first coupling 210 and the second coupling 210 are closed. In other words, the process for uncoupling the first coupling 210 from the second coupling 210 also causes the fluid flow paths through the first coupling 210 and the second coupling 210 to become closed, as described further below.

In some cases, the fluid coupling device 200 is provided to the end user in a sterile condition, or is made to be compatible with sterilization. As used herein, the term "sterilize" means a process of freeing, to a specified degree, a surface or volume from microorganisms. In example embodiments, the sterility of various components can be achieved using one or more sterilization techniques, including gamma irradiation, E-beam, ethylene oxide (EtO), and/or autoclave technologies.

The materials from which one or more of the components of the fluid coupling device 200 are made of include thermoplastics. In particular embodiments, the materials from which the components of the fluid coupling device 200 are made of are thermoplastics, such as, but not limited to, acetal, ABS, polycarbonate, polysulfone, polyether ether ketone, polysulphide, polyester, polyvinylidene fluoride (PVDF), polyethylene, polyphenylsulfone (PP SU; e.g., Radel®), polyetherimide (PEI; e.g., Ultem®), polypropylene, polyphenylene, polyaryletherketone, and the like, and combinations thereof.

In some embodiments, the materials from which one or more of the components of the fluid coupling device 200 are made of include metals such as, but not limited to stainless steel, brass, aluminum, plated steel, and the like. In particular embodiments, the fluid coupling device 200 is metallic-free.

FIGS. 34-38 illustrate various views of the body 220. Because the closure clip 260 can be designed the same as the closure clip 160 described above, the body 220 can include the same structural features for interfacing with the closure clip 260 that the body 120 has for interfacing with the closure clip 160. In addition, because the seal 240 can be designed the same as the seal 140 described above, the body 220 can include the same structural features for interfacing with the seal 240 that the body 120 has for interfacing with the seal 140. The body 220 includes a front face 221.

The body 220 includes a projection 221a and a slot 221b. The projection 221a extends from the front face 221. The body 220 also defines the slot 221b that is sized and shaped to releasably receive the projection 221a. That is, when the fluid coupling device 200 is in the coupled, operative configuration, the projection 221a of the first coupling 210 is disposed within the slot 221b of the second coupling 210, and the projection 221a of the second coupling 210 is disposed within the slot 221b of the first coupling 210.

The body 220 also defines a first through-hole 228a and a second through-hole 228b. When the fluid coupling device 200 is in the coupled, operative configuration, the first through-hole 228a of the first coupling 210 is aligned with the second through-hole 228b of the second coupling 210, and the first through-hole 228a of the second coupling 210 is aligned with the second through-hole 228b of the first coupling 210. When the fluid coupling device 200 is in the coupled, operative configuration, the arms 231a-b of the retainer 230 pass through the aligned: (i) first through-hole 228a of the first coupling 210 and second through-hole 228b of the second coupling 210 and (ii) first through-hole 228a of the second coupling 210 and second through-hole 228b of the first coupling 210. In that manner, the couplings 210 are securely constrained face 221 to face 221 (and seal 240 to seal 240).

In the depicted embodiment, the cross-sectional shapes of the through-holes 228a-b are oblong (e.g., elliptical, oval, race-tracked shaped, etc.). The oblong shape allows the arms 231a-b of the retainer 230 (FIG. 39) to be deflected laterally outward in response to the depression of the closure clips 260 so that the retainer 230 can thereafter be removed from engagement with the bodies 220.

In the depicted embodiment, the body 220 also defines grooves 229a-b that are open to, and extend along, the through-holes 228a-b. The grooves 229a-b slidingly receive ribs 233a-b projecting from the arms 231a-b of the retainer 230 (FIG. 39).

Figure 39:
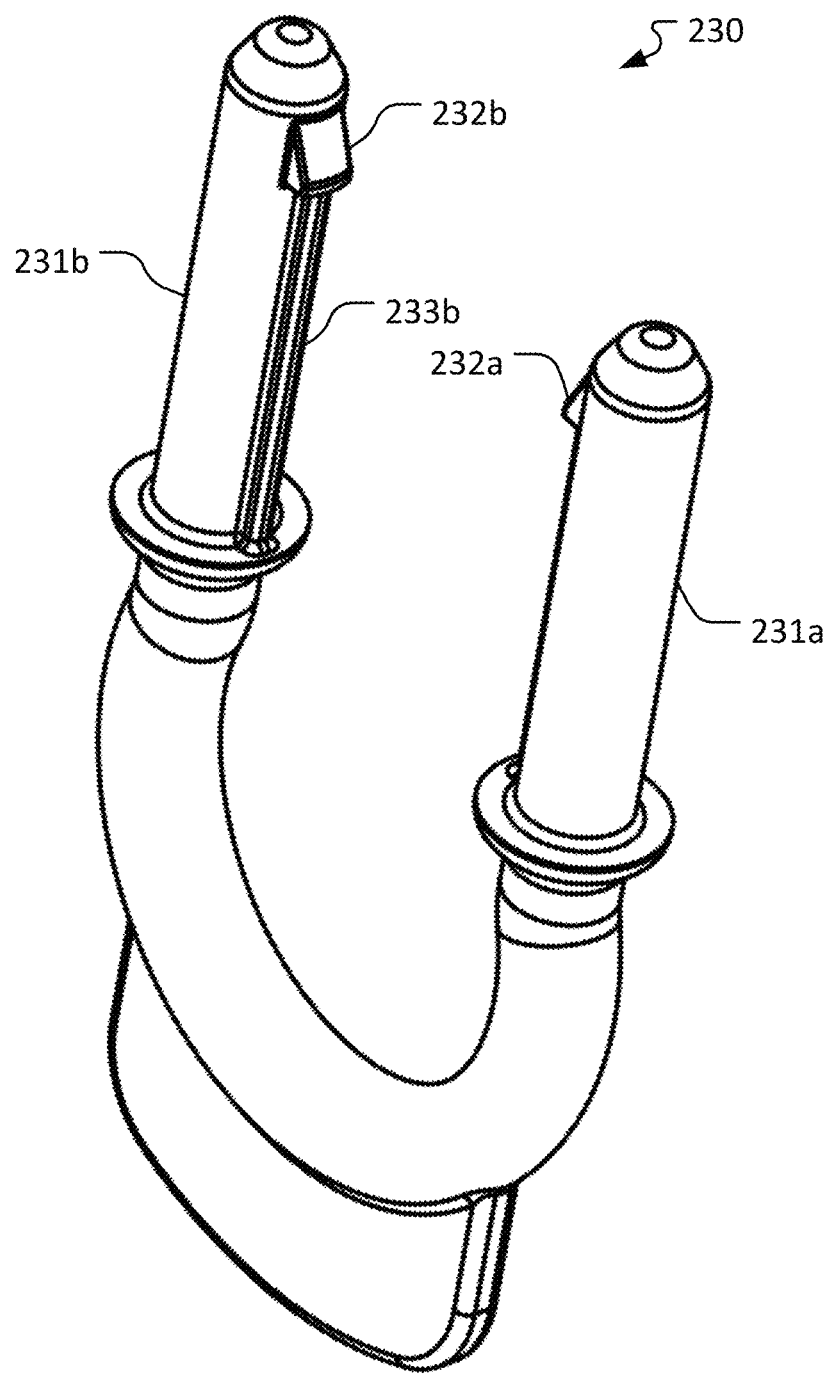
FIG. 39 is a perspective view of a retainer of the fluid coupling device of FIG. 29.

FIG. 39 illustrates the retainer 230. The retainer 230 includes inwardly projecting barbs 232a-b at the free ends of the arms 231a-b. Those barbs 232a-b engage against the bodies 220 to retain the retainer 230 in engagement with the bodies 220 until the closure clips 260 are depressed into the bodies 220. Then, the arms 231a-b are forced to deflect laterally outward and the barbs 232a-b disengage from the bodies 220. Then the retainer 230 can be slid out of the through-holes 228a-b so as to disengage the retainer 230 from the couplings 210.

Figure 40:
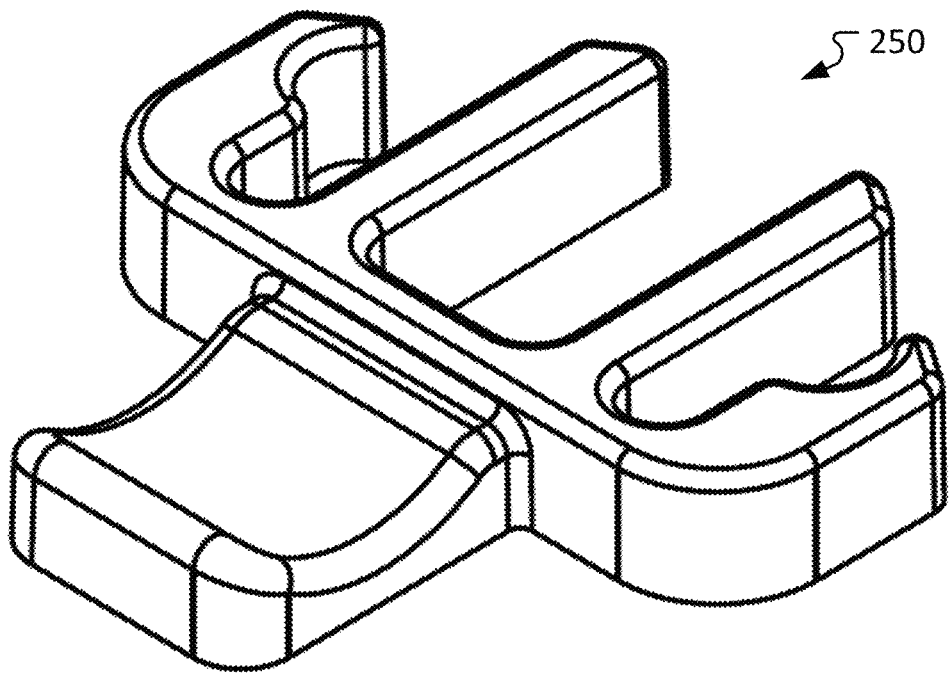
FIG. 40 is a perspective view of a spacer of the fluid coupling device of FIG. 29.
Figure 41:
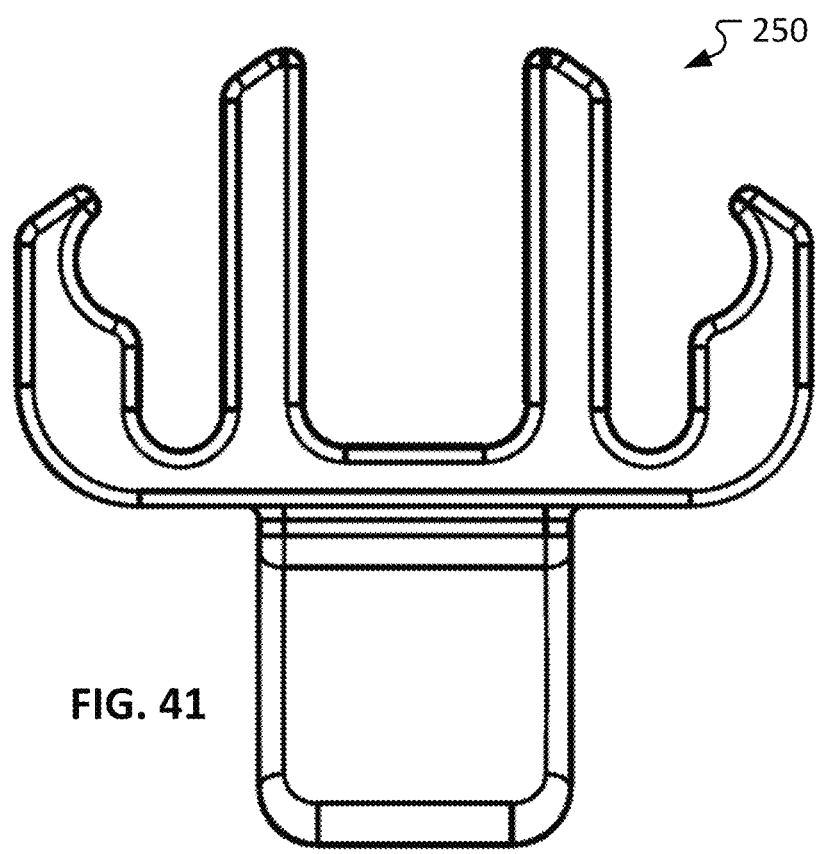
FIG. 41 is a top view of the spacer of FIG. 40.
Figure 42:
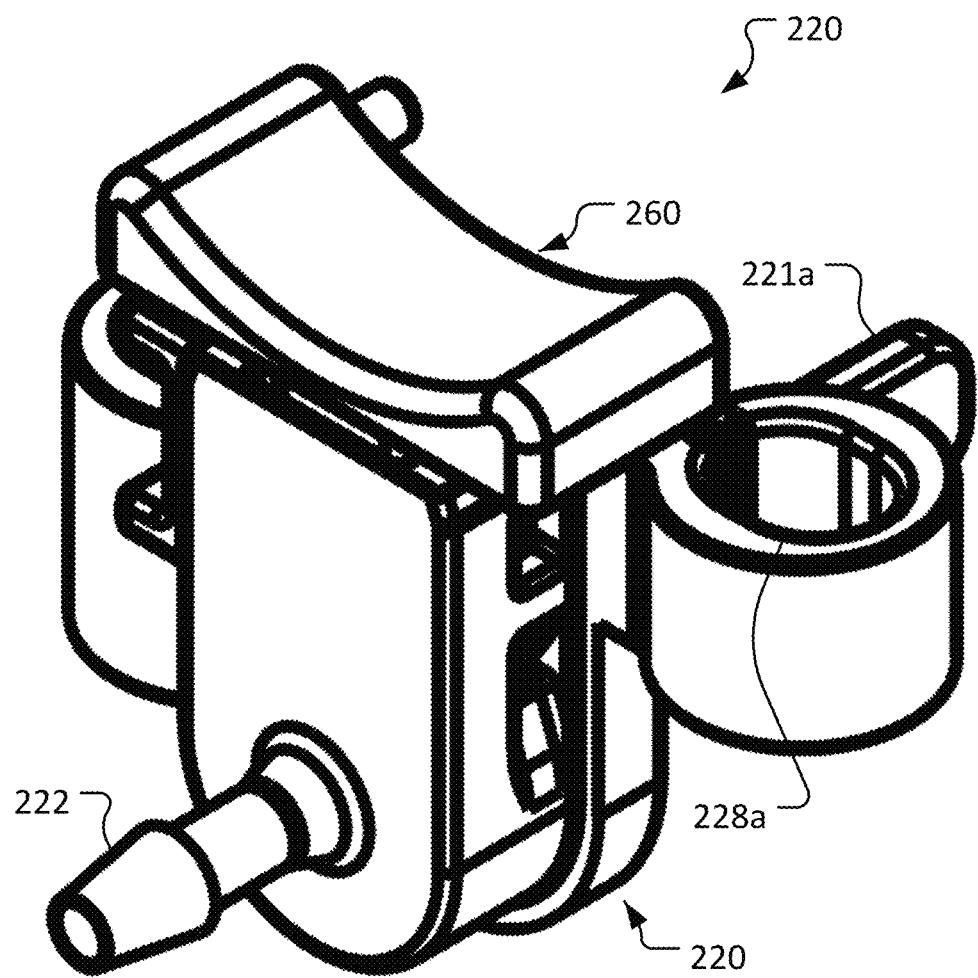
FIG. 42 is a perspective view of a single coupling of the fluid coupling device of FIG. 29.
Figure 43:
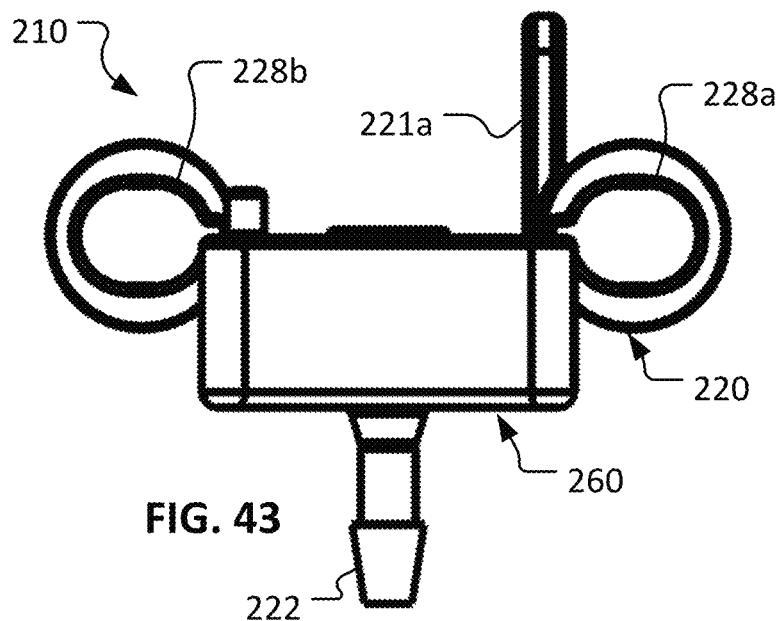
FIG. 43 is a top view of the single coupling of FIG. 42.
Figure 44:
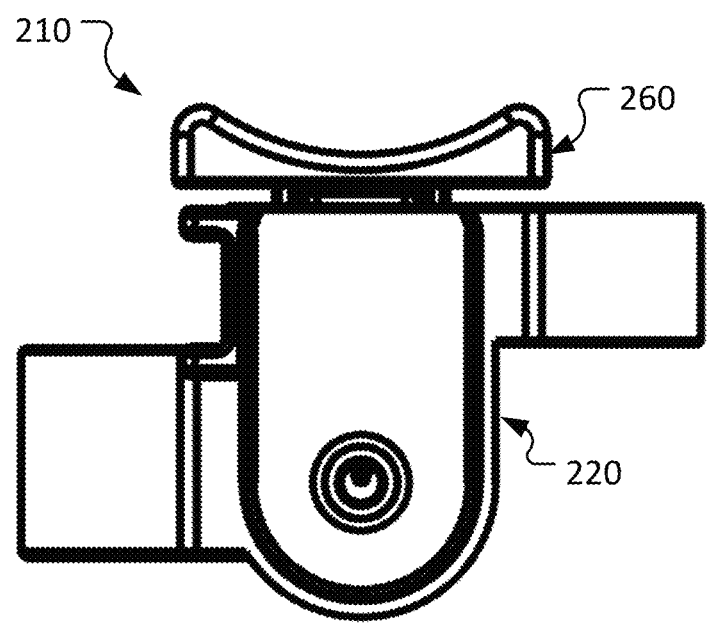
FIG. 44 is an end view of the single coupling of FIG. 42.
Figure 45:
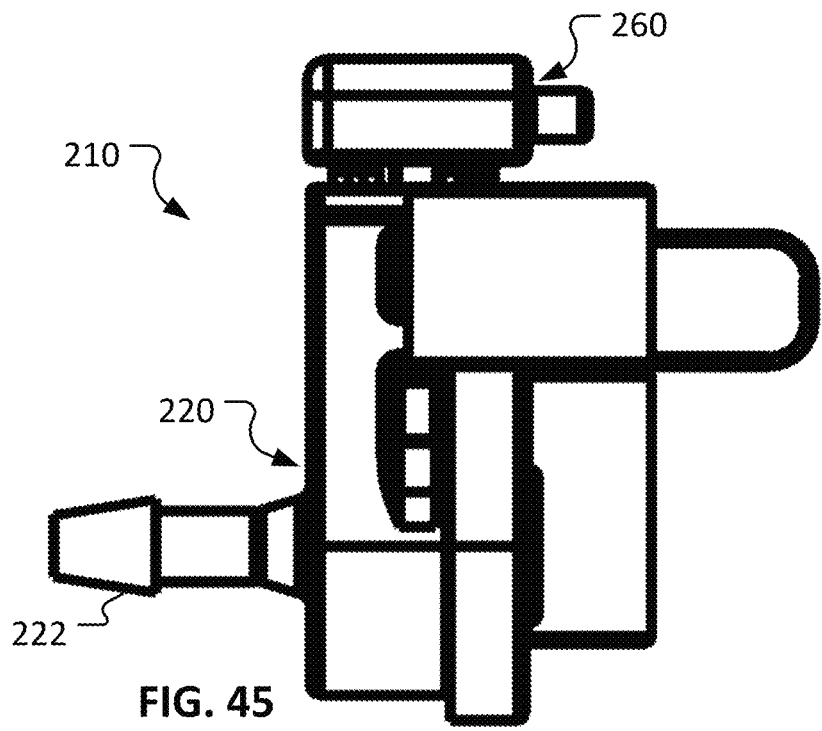
FIG. 45 is a side view of the single coupling of FIG. 42.

FIGS. 40 and 41 illustrate an example spacer 250. The spacer 250, which is optional, must be removed from engagement with the couplings 210 to allow the closure clips 260 to be depressed into the bodies 220. The spacer 250 is a fork-like device with multiple arms and a projection configured for manually grasping the spacer 250. The user can pull the spacer 250 out of engagement with the couplings 210 when it is desired to uncouple the couplings 210 from each other.

FIGS. 42-46 illustrate various view of a single coupling 210 after the fluid coupling device 200 has been reconfigured from the operative, coupled configuration shown in FIGS. 29-33 to an uncoupled configuration in which the retainer 230 has been removed and the two couplings 210 are separated from each other. To transition from the operative, coupled configuration to the uncoupled configuration the following steps are performed by a user. First, the spacer 250 (if included) is pulled away from engagement with the couplings 210.

Figure 46:
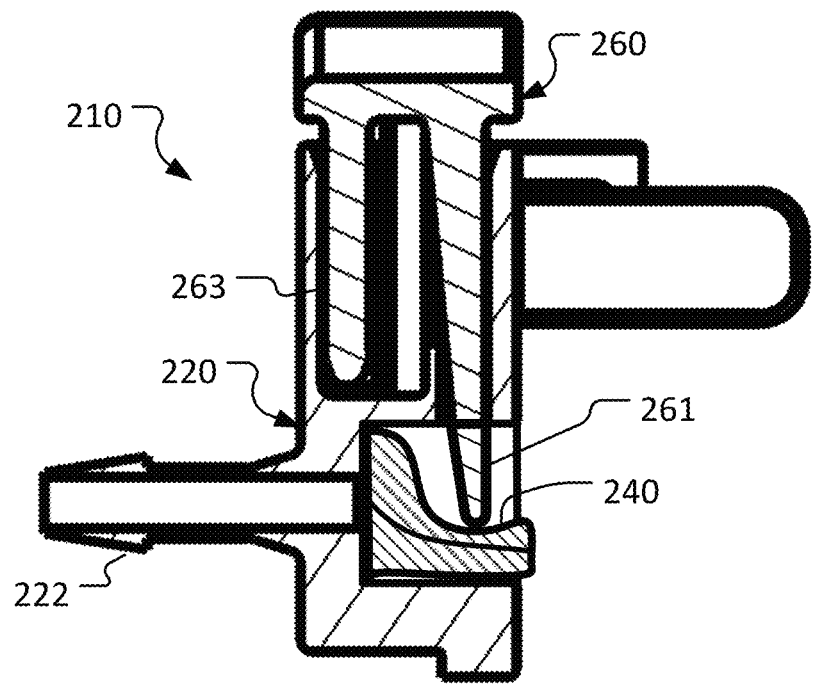
FIG. 46 is a longitudinal cross-sectional view of the single coupling of FIG. 42.
Figure 47:
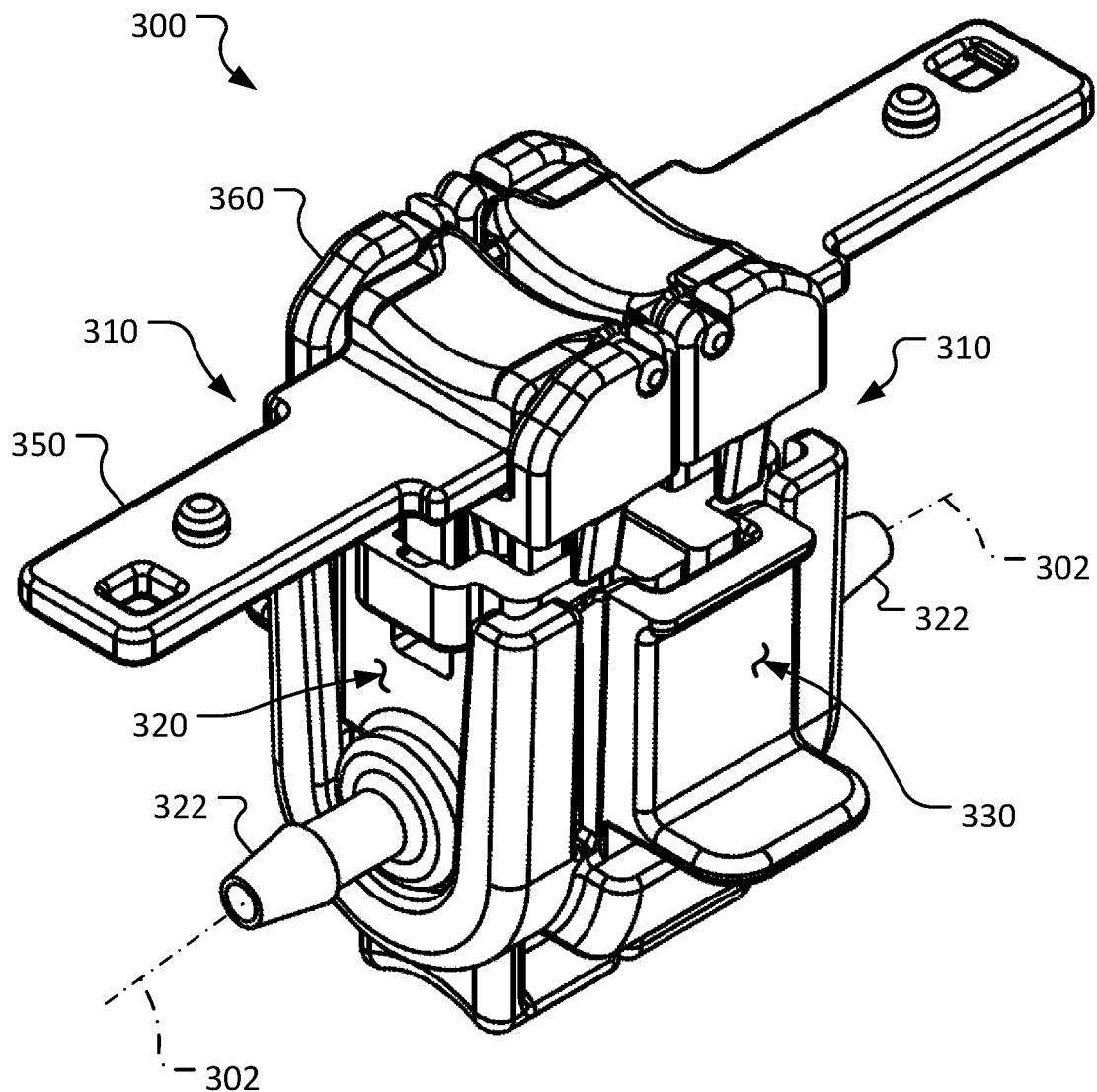
FIG. 47 is a perspective view of another example fluid coupling device in accordance with some embodiments described herein.
Figure 48:
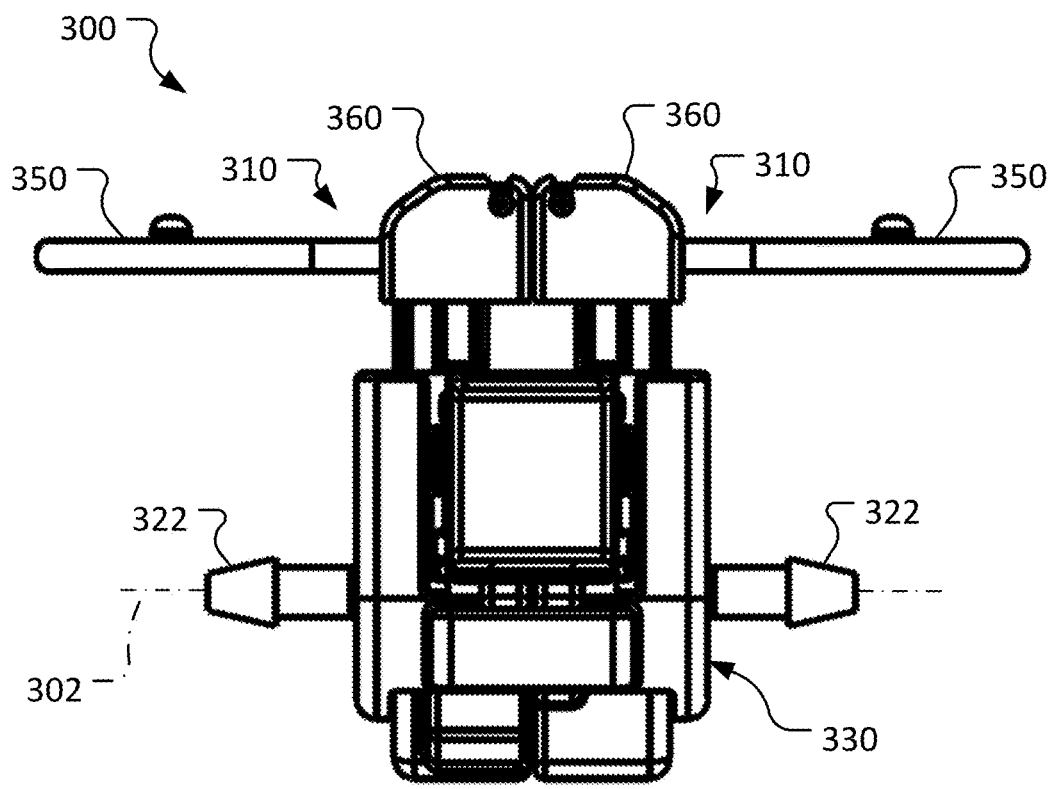
FIG. 48 is a side view of the fluid coupling device of FIG. 47.

Second, the closure clips 260 are depressed into the bodies 220. When the closure clips 260 are fully depressed, the closure clips 260 lock in the depressed orientation relative to the bodies 220 and the projections 261 compress the seals 240 (as shown in FIG. 46) to fully close off the fluid flow paths through the couplings 210. Depressing the closure clips 260 also outwardly flexes the arms 231a-b of the retainer 230 so that the retainer 230 is no longer latched onto the couplings 210.

Third, the retainer 230 can be pulled laterally off from the couplings 210. The retainer 230 can be discarded.

Fourth, the couplings 210 can be separated from each other.

FIGS. 47-52 illustrate another type of fluid coupling device 300 that has essentially the same operational features as the fluid coupling device 100 described above. The main differences are related to the covers 350 and seals 340 (not visible). For example, the covers 150 of the fluid coupling device 100 are pivotably coupled to the bodies 120 (e.g., see FIG. 2). In contrast, the covers 350 of the fluid coupling device 300 are pivotably coupled to the closure clips 360. In addition, the seals 340 are different, as described further below.

The illustrated fluid coupling device 300 broadly includes a first coupling 310, a second coupling 310, and a retainer 330. In the depicted embodiment, the first coupling 310 and the second coupling 310 are substantially identical to each other. Accordingly, the first coupling 310 and second coupling 310 can be considered to be genderless couplings (e.g., substantially identical except for possibly differences in the styles of the terminations 322). However, in some embodiments of the fluid coupling device 300 the first coupling 310 and second coupling 310 are structurally different from each other, as desired.

An open, two-way fluid flow path 301 (FIG. 49) is defined through the fluid coupling device 300, between a first termination 322 of the first coupling 310 and a second termination 322 of the second coupling 310 while the fluid coupling device 300 is in its first configuration as shown (also referred to as the coupled, operative configuration). The fluid flow path 301 extends through the bodies 320 and the bores of the seals 340.

The fluid coupling device 300 can be provided to the end user in the coupled, operative configuration as shown. Then, after use as desired, the fluid coupling device 300 can be reconfigured to separate the first coupling 310 from the second coupling 310. In the separated configuration, the fluid flow paths through the first coupling 310 and the second coupling 310 are closed (e.g., see FIGS. 72-74). In other words, the process for uncoupling the first coupling 310 from the second coupling 310 also causes the fluid flow paths through the first coupling 310 and the second coupling 310 to become closed, as described further below.

Figure 74:
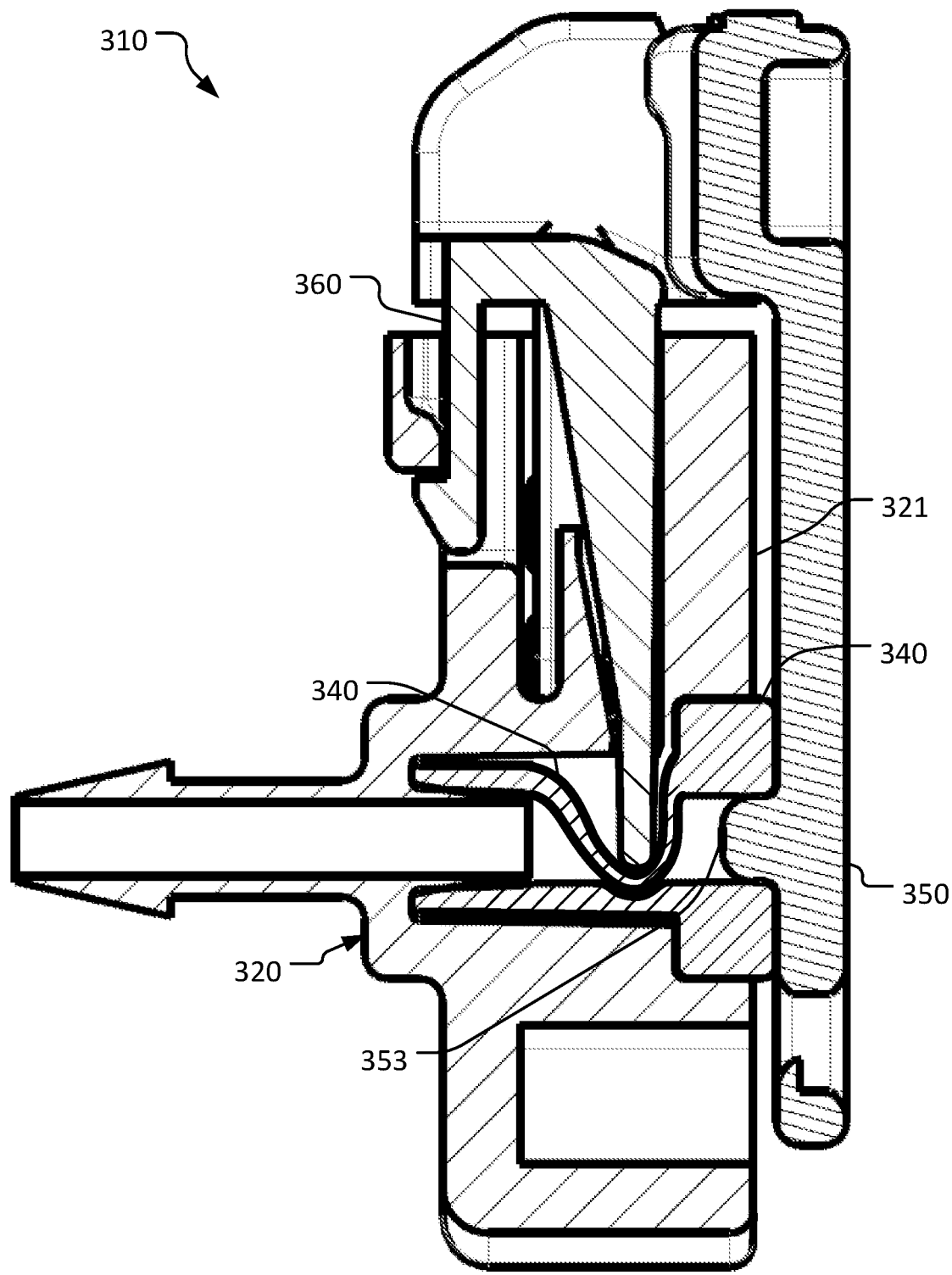
FIG. 74 is a cross-sectional view of the fluid coupling device of FIG. 47 in a closed configuration in which the fluid flow path through the coupling device is fluidly sealed shut.

The process for uncoupling the first coupling 310 from the second coupling 310 includes: (i) depressing the covers 350 and closure clips 360 into the bodies 320 to the point that the closure clips 360 snap into their closed positions relative to the bodies 320 (this pinches the seals 340 closed to prevent fluid flow), (ii) removing the retainer 330, (iii) separating the first coupling 310 from the second coupling 310, and (iv) pivoting the covers 350 closed into their latched positions (this plugs the ends of the seals 340 as shown in FIG. 74).

In some cases, the fluid coupling device 300 is provided to the end user in a sterile condition, or is made to be compatible with sterilization. As used herein, the term "sterilize" means a process of freeing, to a specified degree, a surface or volume from microorganisms. In example embodiments, the sterility of various components can be achieved using one or more sterilization techniques, including gamma irradiation, E-beam, ethylene oxide (EtO), and/or autoclave technologies.

The materials from which one or more of the components of the fluid coupling device 300 are made of include thermoplastics and/or thermosets. In particular embodiments, the materials from which the components of the fluid coupling device 300 are made of are thermoplastics, such as, but not limited to, acetal, ABS, polycarbonate, polysulfone, polyether ether ketone, polysulphide, polyester, polyvinylidene fluoride (PVDF), polyethylene, polyphenylsulfone (PPSU; e.g., Radel®), polyetherimide (PEI; e.g., Ultem®), polypropylene, polyphenylene, polyaryletherketone, and the like, and combinations thereof. In some embodiments, the thermoplastics can include one or more fillers such as, but not limited to, glass fiber, glass bead, carbon fiber, talc, etc.

In some embodiments, the materials from which one or more of the components of the fluid coupling device 300 are made of include metals such as, but not limited to stainless steel, brass, aluminum, plated steel, and the like. In particular embodiments, the fluid coupling device 300 is metallic-free.

In certain embodiments, fluid coupling assembly 300 includes one or more gaskets or seals (e.g., the seals 340) that are made of materials such as, but not limited to, silicone, fluoroelastomers (FKM), ethylene propylene diene monomer (EPDM), thermoplastic elastomers (TPE), buna, buna-N, thermoplastic vulcanizates (TPV), and the like. In some embodiments, a portion of the gaskets or seals can have a cross-sectional shape that is an hourglass-shape, an oval shape, a circular shape, D-shaped, X-shaped, square, rectangular, U-shaped, a polygonal shape, a multi-lobe shape, or any other suitable shape, without limitation.

FIGS. 53-56 show the body 320 in isolation so that greater detail of the body 320 can be visualized. The body 320 has a front face 321. In the coupled configuration of the fluid coupling device 300, the two bodies 320 have their front faces 321 abutting against each other.

Figure 49:
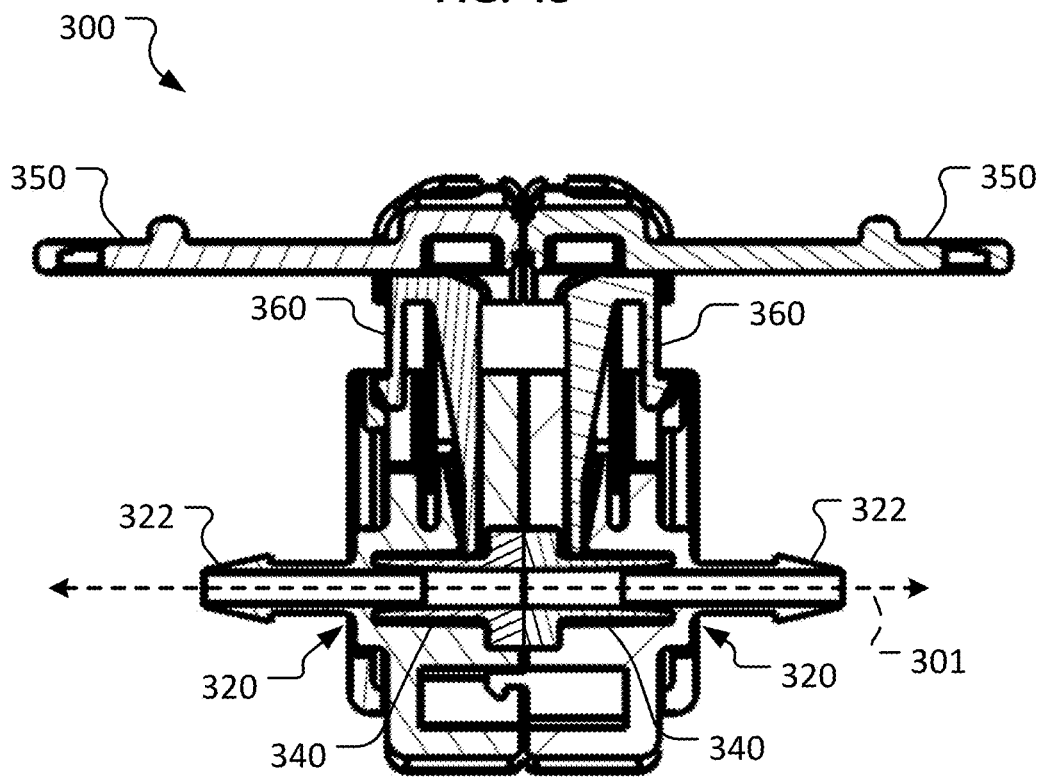
FIG. 49 is a longitudinal cross-section view of the fluid coupling device of FIG. 47.
Figure 50:
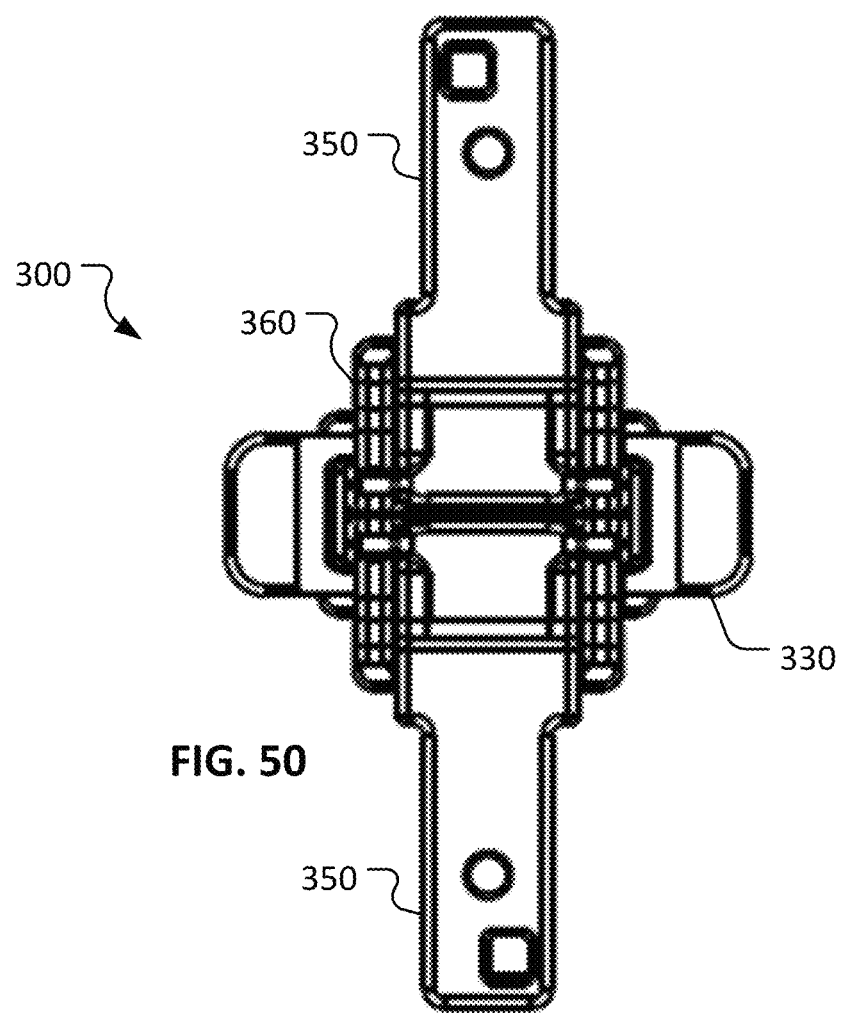
FIG. 50 is a top view of the fluid coupling device of FIG. 47.
Figure 51:
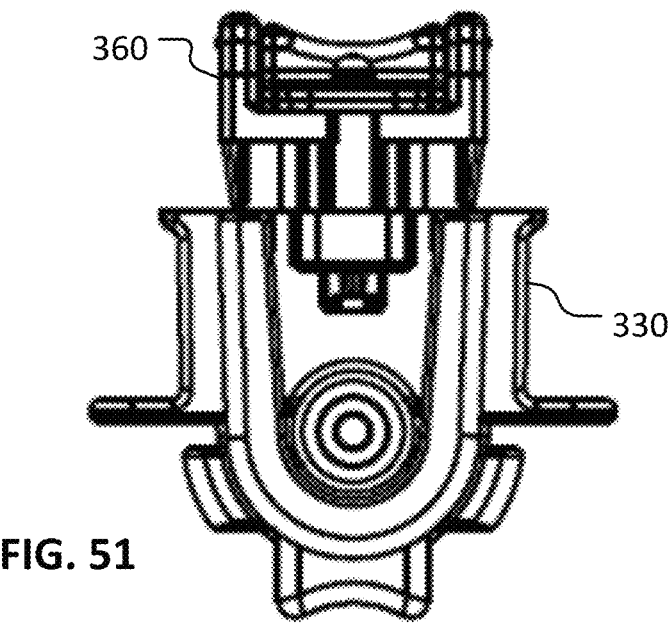
FIG. 51 is an end view of the fluid coupling device of FIG. 47.
Figure 52:
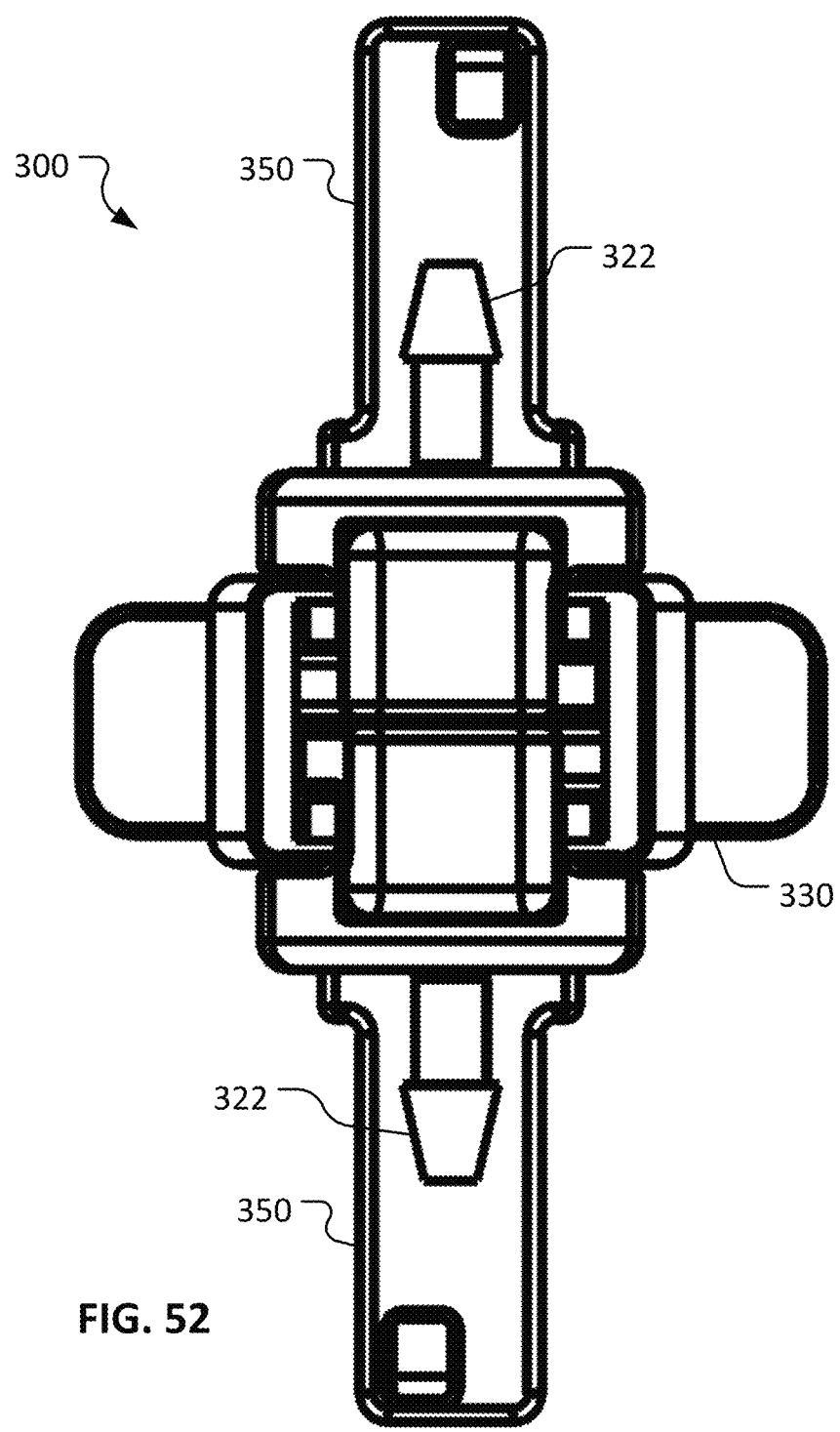
FIG. 52 is a bottom view of the fluid coupling device of FIG. 47.
Figure 53:
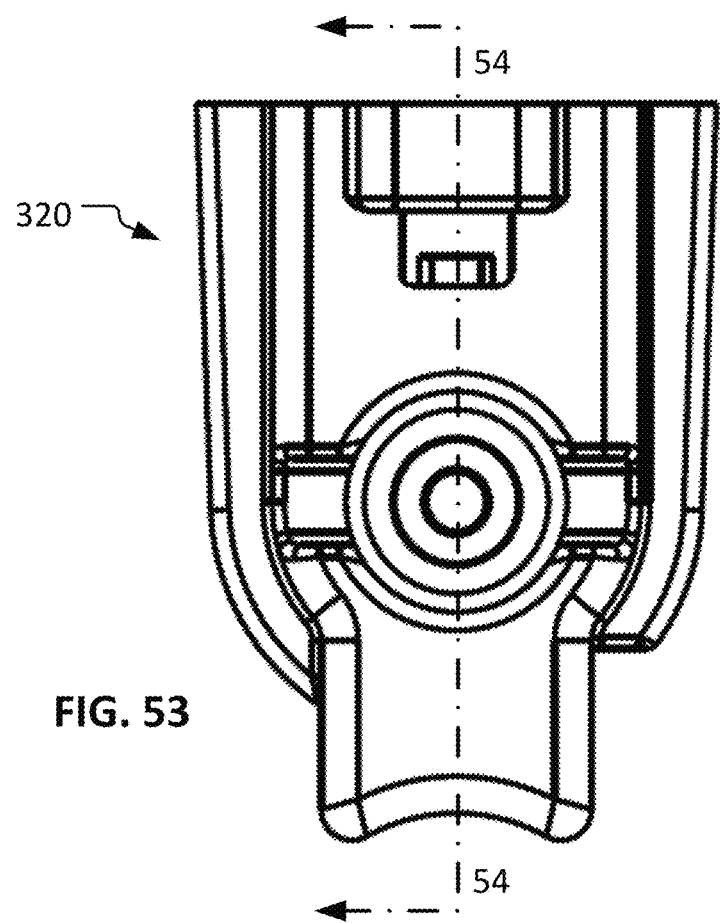
FIG. 53 is an end view of a main body of the fluid coupling device of FIG. 47.
Figure 54:
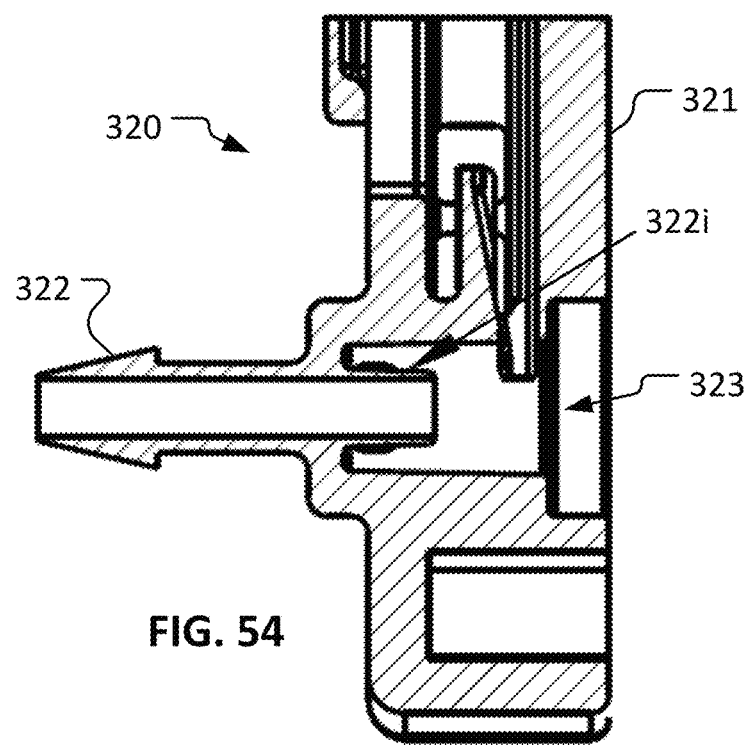
FIG. 54 is a cross-section view of the main body of FIG. 53.
Figure 55:
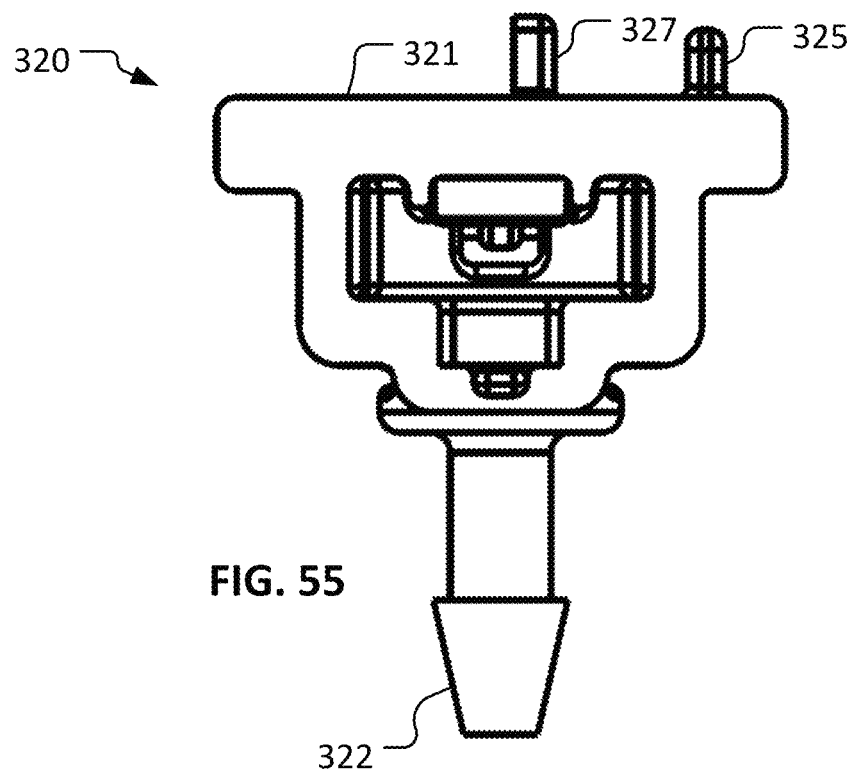
FIG. 55 is a top view of the main body of FIG. 53.
Figure 56:
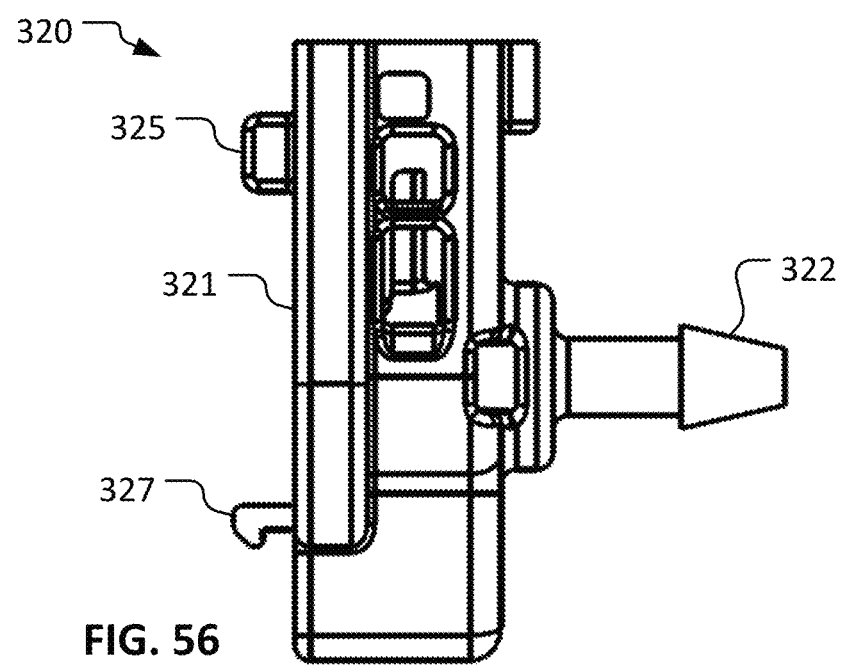
FIG. 56 is a side view of the main body of FIG. 53.
Figure 57:
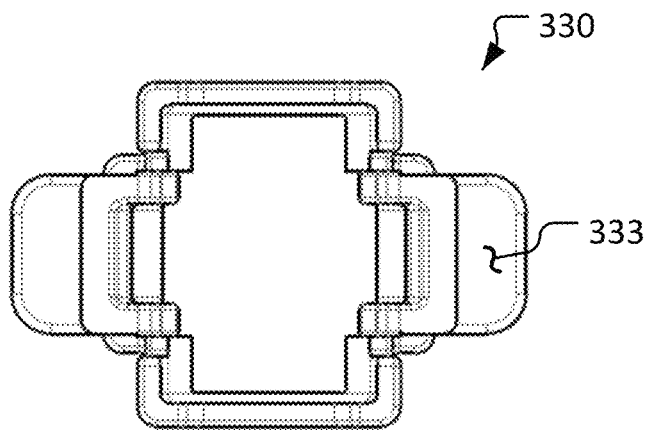
FIGS. 57-60 are various views of a retainer of the fluid coupling device of FIG. 47.
Figure 58:
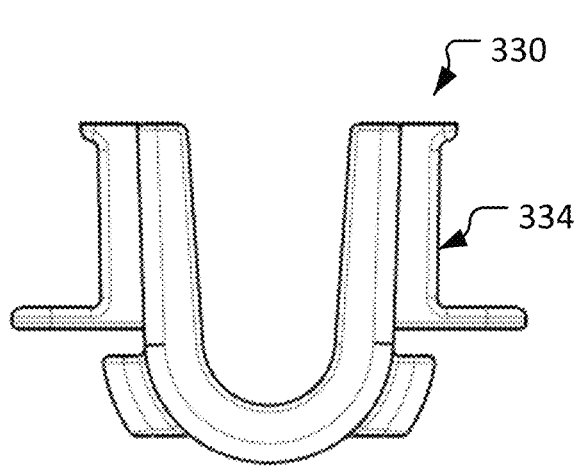
Figure 60:
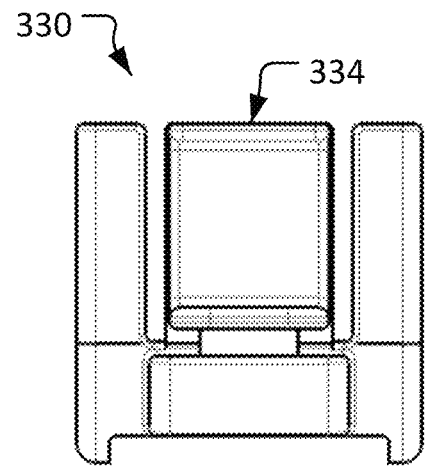
Figure 59:
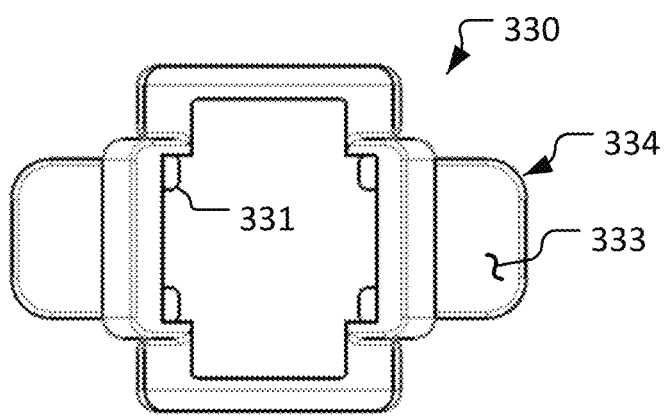
Figure 72:
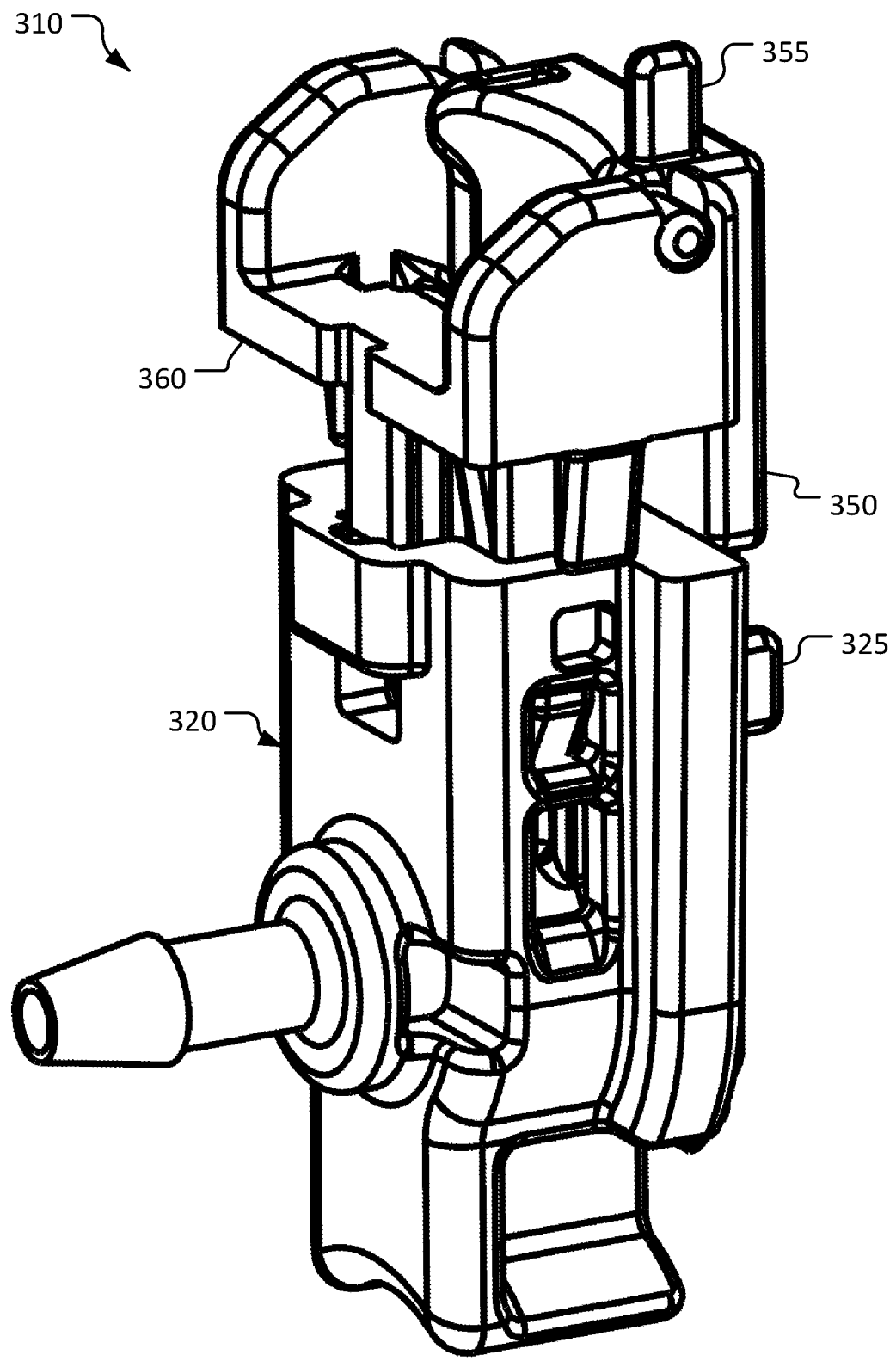
FIGS. 72 and 73 are perspective views of the fluid coupling device of FIG. 47 in a closed configuration in which the fluid flow path through the coupling device is fluidly sealed shut.
Figure 73:
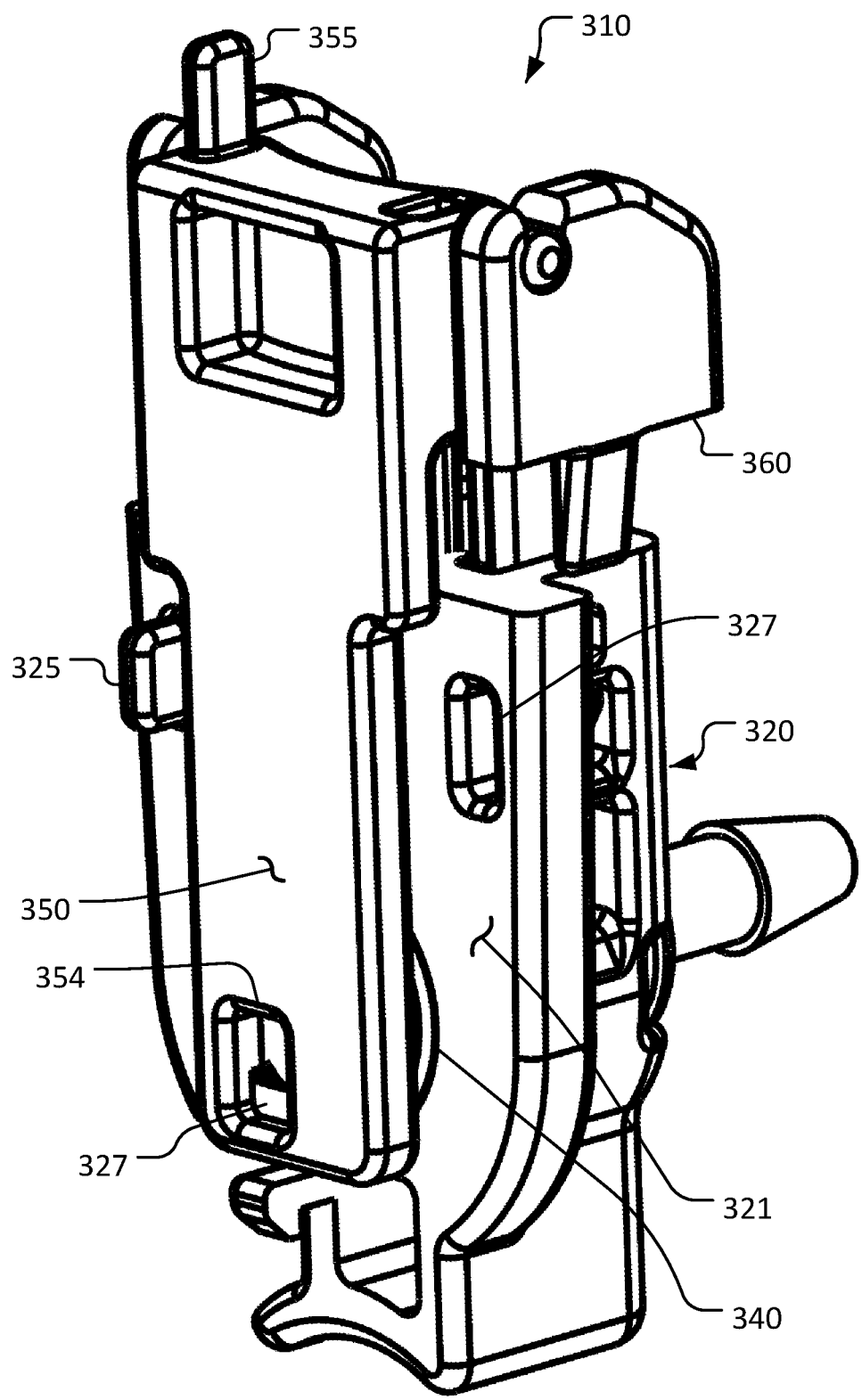

The closure clip 360 (e.g., see FIGS. 61 and 62) is slidingly engaged with the body 320. The body 320 and the closure clip 360 include complementary features that allow the closure clip 360 to be latched in two different positions relative to the body 320. The first position is as shown in FIG. 49, for example. In the first position, the fluid flow path 301 is open. The second position is as shown in FIGS. 72-74, for example, when the closure clip 360 has been depressed into deeper engagement with the body 320. In that second position, the closure clip 360 pinches the seal 340 closed. The closure clip 360 latches with the body 320 in the second position.

Figure 71:
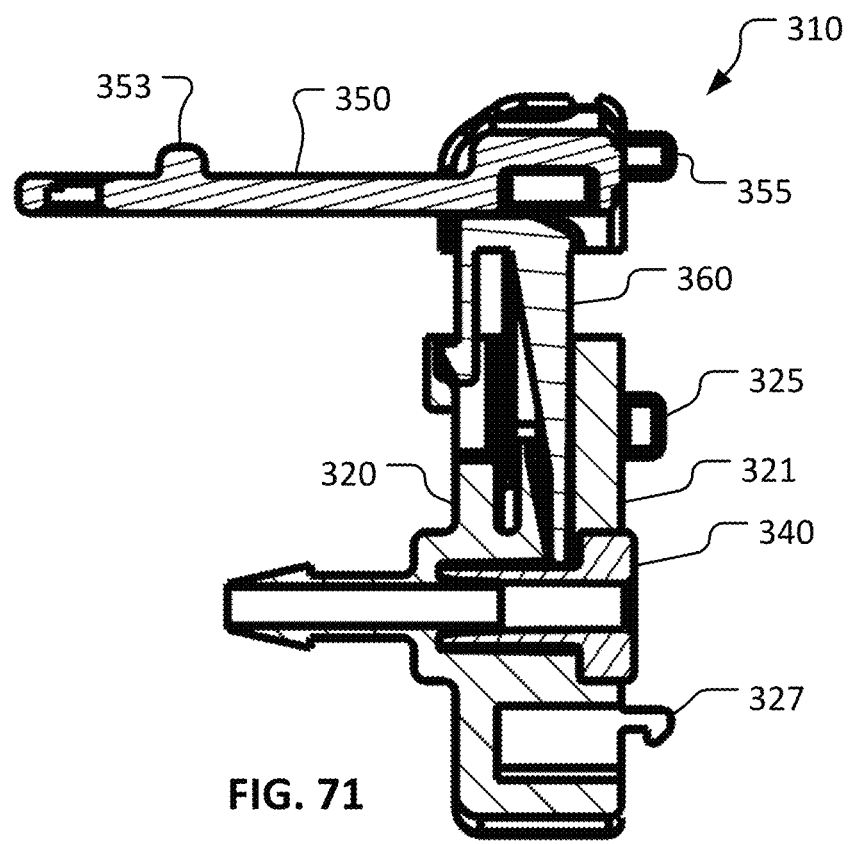

The body 320 defines a seal recess 323. The seal recess 323 is shaped to snuggly receive the seal 340 (FIG. 72). When the seal 340 is seated in the seal recess 323, an outer end portion 342 of the seal 340 (FIGS. 65-67) projects out from the front face 321 of the body 320 (e.g., see FIG. 71). Accordingly, when the fluid coupling device 300 is in the coupled configuration the seals 340 of the first and second couplings 310 are compressed against each other (which creates a fluid seal therebetween).

The body 320 also includes an internal nipple 322i (e.g., see FIG. 54) that projects into the seal recess 323. An inner end portion 344 of the seal 340 (FIGS. 65-67) is in sealed engagement on the internal nipple 322i (e.g., see FIGS. 49, 71, and 74).

The body 320 includes a post 325 that projects from the front face 321. The post 325 slidingly engages in a recess 327 (e.g., see FIG. 69) defined by the body 320 when two of the bodies 320 are arranged in the coupled configuration with the front face 321 of the first coupling 310 abutted against front face 321 of the second coupling 310.

Figure 68:
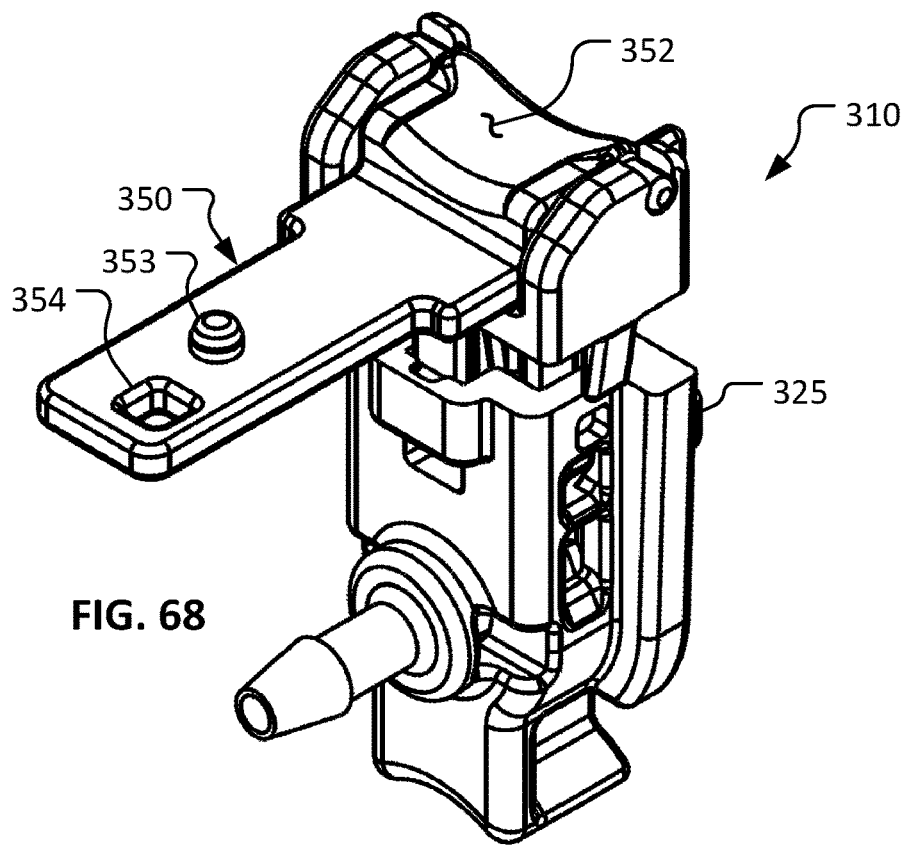
FIGS. 68-71 are various views of a fluid coupling of the fluid coupling device of FIG. 47.

The body 320 also includes a hook 327 that projects from the front face 321. The hook 327 engages with an opening 354 (e.g., see FIGS. 64, 68, and 69) defined by the cover 350 to latch the cover 350 in its closed position relative to the body 320 as shown in FIGS. 72-74.

FIGS. 57-60 show the retainer 330 in isolation so that greater detail of the retainer 330 can be visualized. The retainer 330 is configured to compress the first coupling 310 and the second coupling 310 together in a fluid-tight arrangement. The retainer 330 is generally U-shaped (e.g., see FIG. 58) with an open bottom.

The retainer 330 is releasably latched to the first coupling 310 and the second coupling 310 when the fluid coupling device 300 is in its coupled operative configuration (e.g., see FIGS. 47-52) which is also called its first configuration. In particular, the retainer 330 includes two flexible side portions 334 that include one or more projections 331. The one or more projections 331 are releasably engaged with recesses defined by the bodies 320 while the fluid coupling device 300 is in its coupled operative configuration. Then, when the closure clips 360 are depressed into the bodies 320, the closure clips 360 slide against ramps of the two flexible side portions 334 to cause the side portions 334 to deflect outward. The outward deflection disengages the one or more projections 331 from the recesses defined by the bodies 320. That disengagement of the one or more projections 331 from the recesses defined by the bodies 320 allows the retainer 330 to be removed from engagement with the first coupling 310 and the second coupling 310. The side portions 334 conveniently include transversely-extending surfaces 333 that can be manually pushed on to remove (slide) the retainer 330 from engagement with the first coupling 310 and the second coupling 310.

Figure 61:
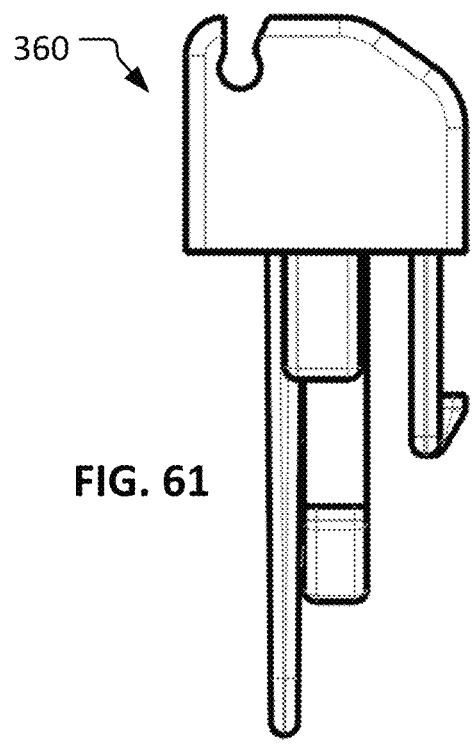
FIG. 61 is a side view of a closure clip of the fluid coupling device of FIG. 47.
Figure 62:
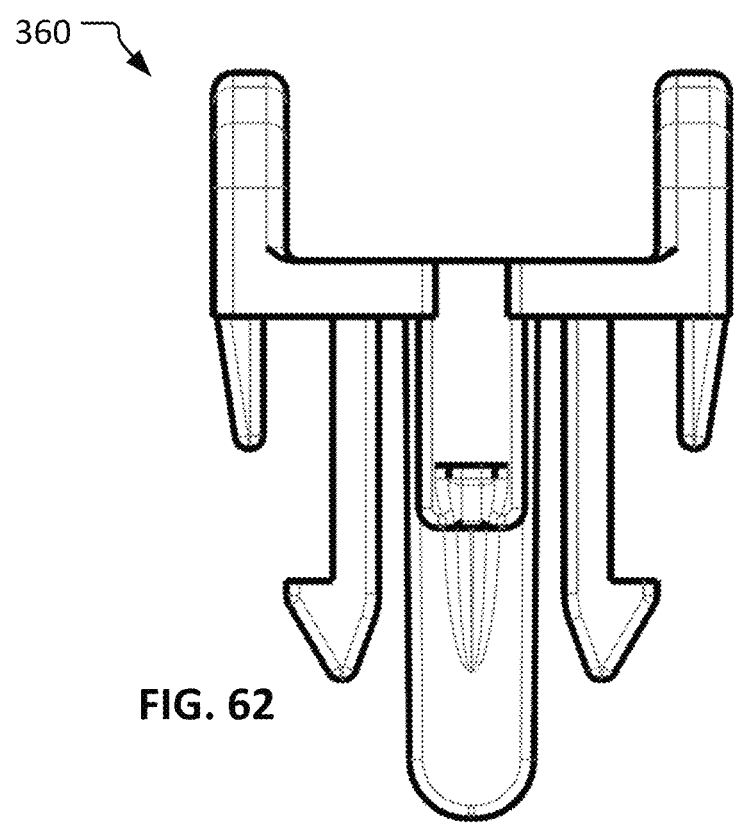
FIG. 62 is an end view of the closure clip of FIG. 61.

FIGS. 61 and 62 show the closure clip 360 in isolation so that greater detail of the closure clip 360 can be visualized. The closure clip 360 has essentially the same features as the closure clip 160 described above (e.g., FIGS. 20-23). One exception is that the closure clip 360 and the cover 350 are pivotably coupled to each other.

Figure 63:
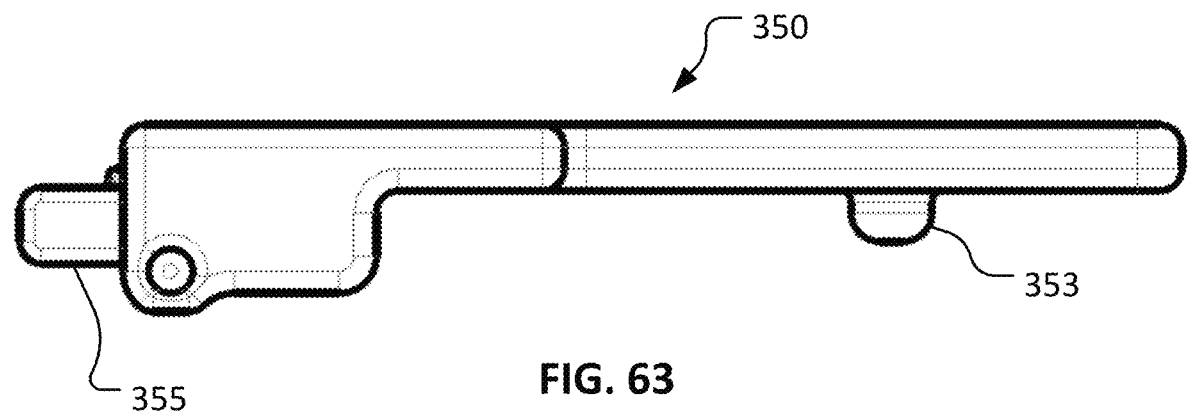
FIG. 63 is a side view of a cover of the fluid coupling device of FIG. 47.
Figure 64:
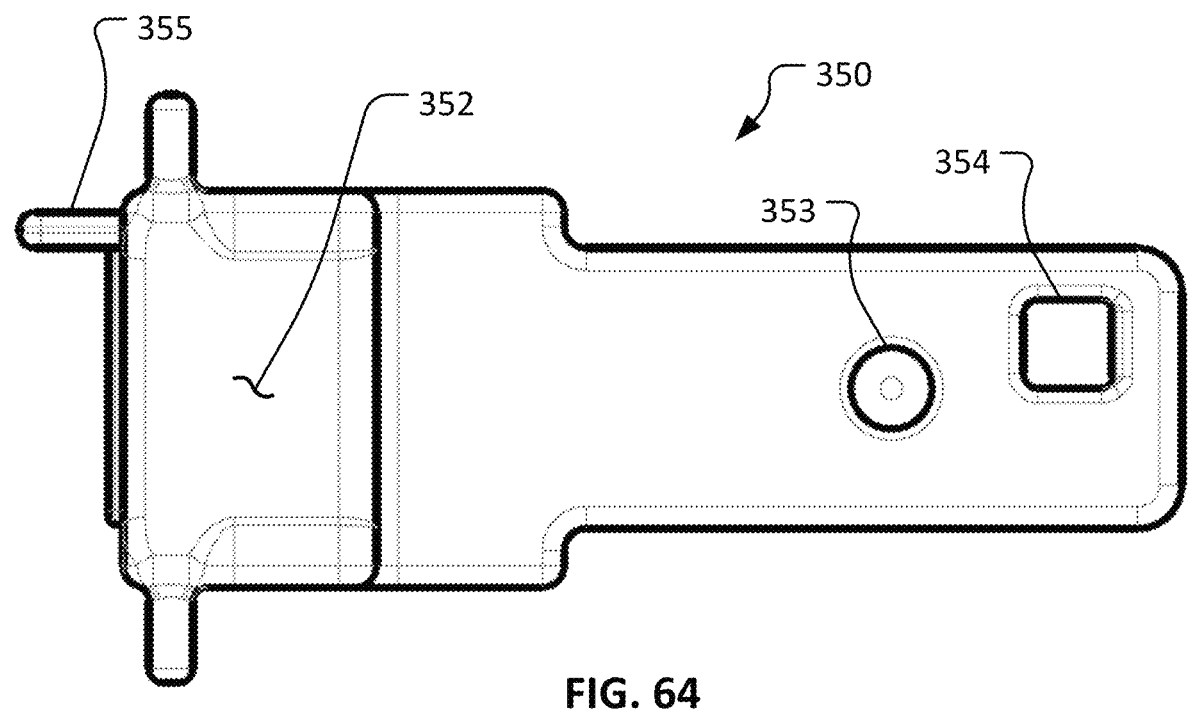
FIG. 64 is a top view of the cover of FIG. 63.

FIGS. 63 and 64 show the cover 350 in isolation so that greater detail of the cover 350 can be visualized. The cover 350 is pivotably coupled to the closure clip 360. The cover 350 includes a contoured surface 352 that is arranged to be pushed on to force the closure clip 360 deeper into the body 320 to pinch closed the seal 340. After the seal 340 is pinched closed, the retainer 330 can be removed, and then the first coupling 310 can be separated from the second coupling 310. After that, the cover 350 can be pivoted to its closed position as shown in FIGS. 72-74. In the depicted embodiment, the cover 350 is pivoted 270° when it is reconfigured from its initial position to its closed position.

In the closed position, a plug 353 that projects from the cover 350 will engage within the end opening of the seal 340 as shown in FIG. 74. Also, the hook 327 that projects from the front face 321 of the body 320 will latch in engagement with the opening 354 defined by the cover 350 to latch the cover 350 in its closed position relative to the body 320.

Figure 69:
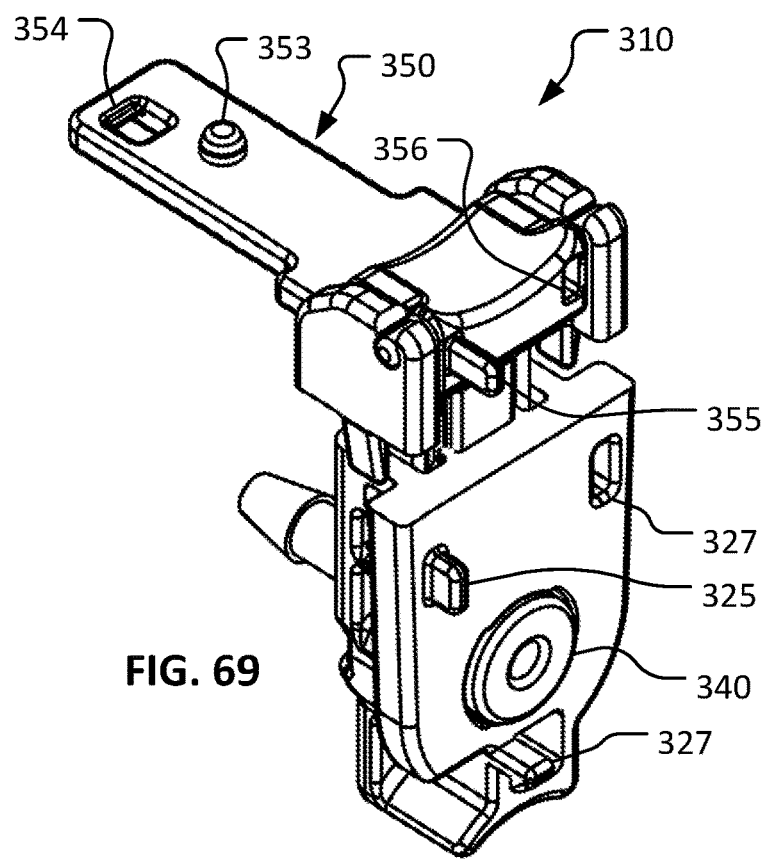
Figure 70:
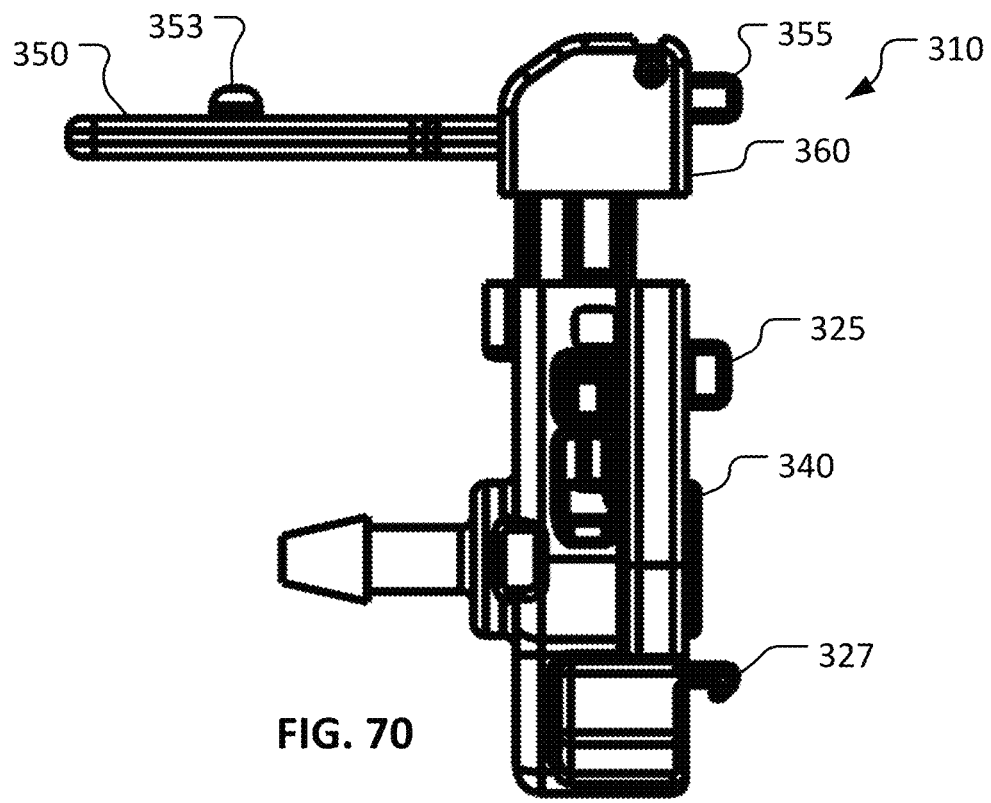

The cover 350 includes a projection 355 and defines a recess 356 (see FIG. 69). When the first coupling 310 and the second coupling 310 are engaged in a face-to-face arrangement, the projection 355 of the first cover 350 is engaged in the recess 356 of the second cover 350, and the projection 355 of the second cover 350 is engaged in the recess 356 of the first cover 350. This engagement between the projections 355 and the recesses 356 releasably interlocks the first cover 350 and the second cover 350. Accordingly, when the contoured surface(s) 352 are pushed on, the first cover 350, the second cover 350, and both of the closure clips 360 move in synchrony. That synchronous movement of the closure clips 360 ensures that the seals 340 of both of the first coupling 310 and the second coupling 310 become fluidly closed prior to separation of the first coupling 310 and the second coupling 310.

Figure 65:
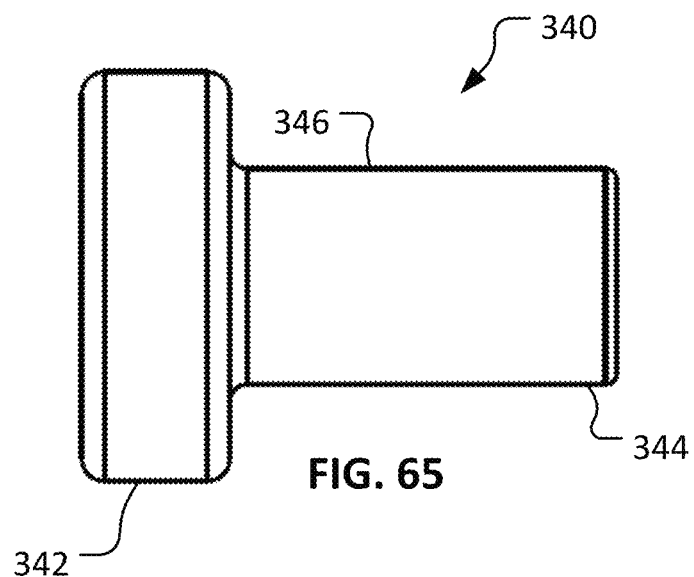
FIG. 65 is a side view of a seal of the fluid coupling device of FIG. 47.
Figure 66:
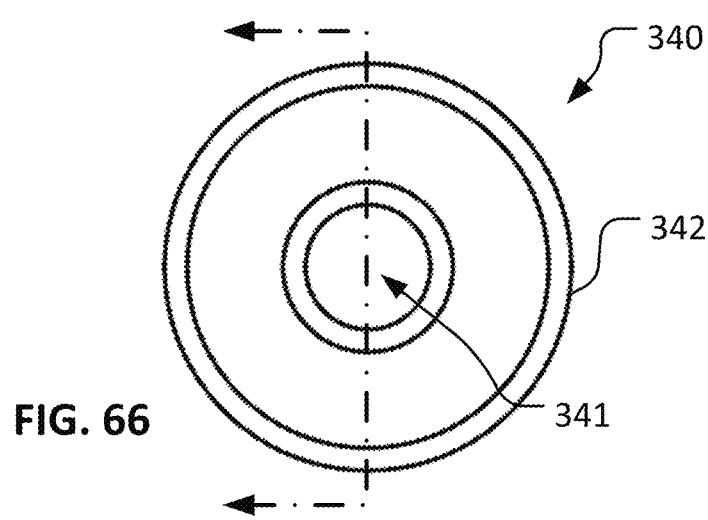
FIG. 66 is an end view of the seal of FIG. 65.
Figure 67:
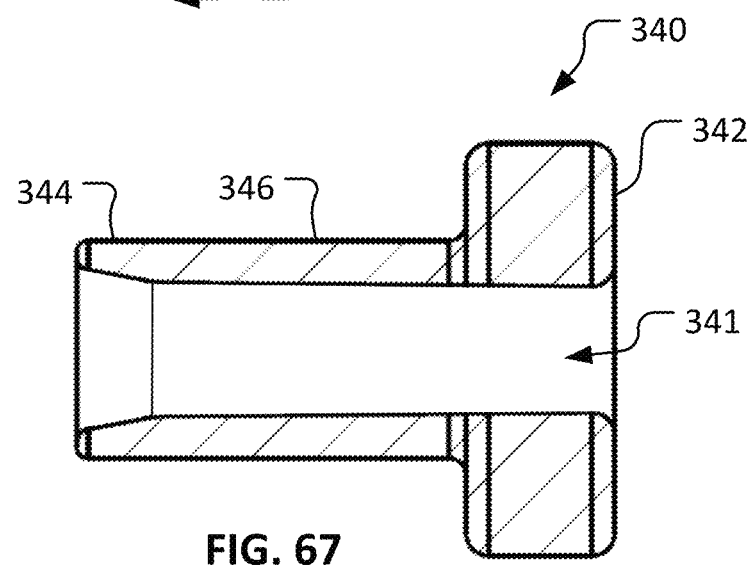
FIG. 67 is a longitudinal cross-section view of the seal of FIG. 65.

FIGS. 65-67 show the seal 340 in isolation so that greater detail of the seal 340 can be visualized. The seal 340 includes an outer end portion 342, an inner end portion 344, and a middle portion 346. The seal 340 defines a bore 341 through the seal 340 between the outer end portion 342 and the inner end portion 344.

In the depicted embodiment, the outer end portion 342 is cylindrical and has a larger outer diameter than the inner end portion 344 and the middle portion 346. The inner diameter of the inner end portion 344 seals in engagement with the internal nipple 322i (FIG. 54) that projects into the seal recess 323 of the body 320.

The middle portion 346 of the seal 340 is flexible. As shown in FIG. 74, the middle portion 346 becomes stretched and compressed to close the bore 341 when the closure clip 360 is depressed into the body 320 to its closed position (reconfiguring the fluid coupling 310 from its first configuration to its second configuration). This fluidly closes the fluid flow path through the fluid coupling 310.

FIGS. 68-71 show the fluid coupling 310 in isolation so that greater detail of the coupling 310 (representative of the first coupling 310 and the second coupling 310) can be visualized. It should be understood that the coupling 310 would not be in the depicted configuration in real use. That is the case because when the first coupling 310 is separated from second coupling 310 (as shown) the closure clip 360 is pinching the seal 340 closed as shown in FIG. 74, for example. Moreover, the cover 350 would be pivoted to its closed position in which the plug 353 would be engaged in the bore 341 of the seal 340.

FIGS. 72-74 show the fluid coupling 310 in its second configuration in which the flow path through the fluid coupling 310 is fluidly sealed closed, and the cover 350 is pivoted to its latched, closed position.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A fluid coupling device, comprising:
   a first coupling comprising:
      a first body including a first termination end portion, the first body defining a first seal recess and a first fluid flow path extending through the first body from the first termination end portion to the first seal recess;
      a first seal disposed within the first seal recess, the first seal defining a first bore through which the first fluid flow path extends; and
      a first closure clip movably coupled to the first body and including a first projection configured to compress the first seal when the first closure clip is pressed into the first body;
   a second coupling comprising:
      a second body including a second termination end portion, the second body defining a second seal recess and a second fluid flow path extending through the second body from the second termination end portion to the second seal recess;
      a second seal disposed within the second seal recess, the second seal defining a second bore through which the second fluid flow path extends; and
      a second closure clip movably coupled to the second body and including a second projection configured to compress the second seal when the second closure clip is pressed into the second body; and a retainer removably coupled to the first coupling and to the second coupling, the retainer holding the first and second couplings in contact with each other such that: (i) the first seal abuts against the second seal and (ii) the first fluid flow path and the second fluid flow path are fluidly connected.

2. The fluid coupling device of claim 1, wherein the fluid coupling device is reconfigurable from a first configuration to a second configuration by depressing the first and second closure clips relative to the first and second bodies, wherein the first bore and the second bore are each fluidly open while the fluid coupling device is in the first configuration, and wherein the first bore and the second bore are each fluidly closed while the fluid coupling device is in the second configuration.

3. The fluid coupling device of claim 2, wherein the fluid coupling device is configured such that, when the fluid coupling device is in the second configuration, the fluid coupling device is irreversibly configured in the second configuration.

4. The fluid coupling device of claim 2, wherein, while the fluid coupling device is in the second configuration, the first projection compresses the first seal to fluidly close the first bore and the second projection compresses the second seal to fluidly close the second bore.

5. The fluid coupling device of claim 2, wherein the retainer is not removable from the first and second couplings while the fluid coupling device is in the first configuration, and wherein the retainer is removable from the first and second couplings while the fluid coupling device is in the second configuration.

6. The fluid coupling device of claim 5, wherein the first coupling and the second coupling are only separable from each other when: (i) the fluid coupling device is in the second configuration and (ii) the retainer is uncoupled from the first coupling and the second coupling.

7. The fluid coupling device of claim 1, further comprising:
a first cover that is movably coupled to the first body or to the first closure clip; and
a second cover that is movably coupled to the second body or to the second closure clip.

8. The fluid coupling device of claim 7, wherein the fluid coupling device is configured such that when the first and second couplings are separated from each other:
the first cover can be moved to cover the first seal within the first seal recess; and
the second cover can be moved to cover the second seal within the second seal recess.

9. The fluid coupling device of claim 1, wherein the first and second couplings are identical.

10. The fluid coupling device of claim 1, wherein the first and second closure clips are removably coupled to each other such that the first and second closure clips are configured to move synchronously relative to the first body and the second body.

11. The fluid coupling device of claim 1, further comprising a spacer removably coupled to the fluid coupling device and arranged to prevent relative movement between: (i) the first closure clip and the first body, and (ii) the second closure clip and the second body.

12. The fluid coupling device of claim 1, wherein the first and second seal recesses are each shaped as a cylinder and include two open side adjuncts positioned radially of the cylinder.

13. The fluid coupling device of claim 1, wherein the first and second seals each comprise two cylindrical end portions and a central portion with a thinner wall than the two cylindrical end portions, wherein the central portion has an arcuate outer profile and an arcuate inner profile, and wherein a center of an arc of the arcuate outer profile is located in an opposite direction in comparison to a center of an arc of the arcuate inner profile.

14. The fluid coupling device of claim 1, wherein the first seal comprises a cylindrical end portion that has a larger outer diameter than other portions of the first seal.

15. The fluid coupling device of claim 1, wherein the first seal is engaged with an inner nipple of the first body and the second seal is engaged with an inner nipple of the second body.

16. The fluid coupling device of claim 1, further comprising:
a first cover that is movably coupled to the first closure clip; and
a second cover that is movably coupled to the second closure clip.

17. The fluid coupling device of claim 16, wherein the first cover includes a projection that is engaged within a recess defined by the second cover, and wherein the second cover includes a projection that is engaged within a recess defined by the first cover.

18. The fluid coupling device of claim 16, wherein the first cover includes a first plug that projects from the first cover and is configured to fluidly seal the first bore, and wherein the second cover includes a second plug that projects from the second cover and is configured to fluidly seal the second bore.

19. The fluid coupling device of claim 1, wherein the retainer comprises one or more flexible side portions that each include one or more projections that are engaged in one or more corresponding recesses defined by the first and second bodies.

20. The fluid coupling device of claim 19, wherein the one or more projections disengage from the one or more recesses by depressing the first and second closure clips relative to the first and second bodies.

* * * * *